US008165818B2

(12) United States Patent
Nicholls

(10) Patent No.: US 8,165,818 B2
(45) Date of Patent: Apr. 24, 2012

(54) METHOD AND APPARATUS FOR SEARCHING MOLECULAR STRUCTURE DATABASES

(75) Inventor: Anthony Nicholls, Santa Fe, NM (US)

(73) Assignee: OpenEye Scientific Software, Inc., Santa Fe, NM (US)

( * ) Notice: Subject to any disclaimer, the term of this patent is extended or adjusted under 35 U.S.C. 154(b) by 747 days.

(21) Appl. No.: 11/378,758

(22) Filed: Mar. 17, 2006

(65) Prior Publication Data

US 2006/0178840 A1    Aug. 10, 2006

Related U.S. Application Data

(60) Division of application No. 09/644,937, filed on Aug. 23, 2000, now Pat. No. 7,110,888, which is a continuation of application No. PCT/US99/04343, filed on Feb. 26, 1999.

(60) Provisional application No. 60/076,077, filed on Feb. 26, 1998.

(51) Int. Cl.
G06F 19/00 (2011.01)
G06F 15/00 (2006.01)
G06F 7/00 (2006.01)
G11C 17/00 (2006.01)

(52) U.S. Cl. ............ 702/19; 700/1; 365/94; 707/602

(58) Field of Classification Search .................. None
See application file for complete search history.

(56) References Cited

U.S. PATENT DOCUMENTS

| 4,855,931 A | 8/1989 | Saunders | 364/499 |
|---|---|---|---|
| 5,025,388 A | 6/1991 | Cramer, III et al. | 364/496 |
| 5,187,796 A | 2/1993 | Wang et al. | |
| 5,526,281 A | 6/1996 | Chapman et al. | 364/496 |
| 5,703,792 A | 12/1997 | Chapman | 364/496 |
| 6,070,127 A | 5/2000 | Hirono et al. | 702/27 |
| 6,185,506 B1 | 2/2001 | Cramer et al. | 702/19 |
| 6,240,374 B1 | 5/2001 | Cramer et al. | 703/11 |

FOREIGN PATENT DOCUMENTS

WO  WO 97/27559  7/1997

OTHER PUBLICATIONS

Willett et al. Implementation of Nonhierarchic Cluster Analysis Methods in Chemical Information Systems: Selection of Compounds for Biological Testing and Clustering of Substructure Search Output Journal of Chemical and Information Computer Science vol. 26, pp. 109-118 (1986).*
Apaya et al., 1995, "The matching of electrostatic extrema: A useful method in drug design? A study of phosphodiesterase III inhibitors," *Journal of Computer-Aided Molecular Design* 9:33-43.
Arteca et al., 1988, "Shape group studies of molecular similarity: relative shapes of Van der Waals and electrostatic potential surfaces of nicotinic agonists," *J. Mol. Graphics* 6:45-53.
Artymiuk et al., 1992, "Similarity searching in databases of three-dimensional molecules and macromolecules," *J. Chem. Inf. Comput. Sci.* 32(6):617-630.
Barros et al., "Using the triangle inequality to reduce the number of comparisons required for similarity-based retrieval," In: *Proceedings of IS&T/SPIE: Storage and Retrieval for Still Image and Video Databases IV*, Jan. 28-Feb. 2, 1996, vol. 2670, pp. 392-403.
Bath et al., 1994, "Similarity searching in files of three-dimensional chemical structures: Comparison of fragment-based measures of shape similarity," *J. Chem. Inf. Comput. Sci.* 34:141-147.
Bradley et al., 1993, "Deducing molecular similarity using voronoi binding sites," *J. Chem. Inf. Comput. Sci.* 33:750-755
Carbo et al., 1980, "How similar is a molecule to another? An electron density measure of similarity between two molecular structures," *International Journal of Quantum Chemistry* XVII:1185-1189.
Ciaccia et al., "M-tree: An efficient access method for similarity search in metric spaces," In: Proc. 23rd VLDB Conf., Jarke, M., Carey, M.J., Dittrich, K,R., Lochovsky, F.H., Loucopoulos, P., and Jeusfeld, M.A., eds., Athens, Greece, Aug. 1997, pp.426-435.
Cioslowski and Nanyakkara, 1993, "Similarity of atoms in molecules," *J. Am. Chem. Soc.* , 115:11213-11215.
Clarkson, 1997, "Nearest neighbor queries in metric spaces," Proc. 29th ACM Symp. Theory Comp., pp. 609-617.
Constans et al., 1997, "Toward a global maximization of the molecular similarity function: Superposition of two molecules," J. Comput. Chem. 18(6):826-846.
Cramer, III et al., 1974, "Substructural analysis. A novel approach to the problem of drug design," Journal of Medicinal Chemistry 17(5):533-535.
Doman et al., 1996, "Algorithm5: A technique for fuzzy similarity clustering of chemical inventories," *J. Chem. Inf. Comput. Sci.* 36(6):1195-1204.
Drefahl and Reinhard, 1993, "Similarity-based search and evaluation of environmentally relevant properties for organic compounds in combination with the group contribution approach," J. Chem. Inf. Comput. Sci. 33(6):886-895.
Dughan et al., 1991, "The study of peptide bond isosteres using molecular similarity," Journal of Molecular Structure (Theochem) 235:481-488.
Feustel and Shapiro, 1982, "The nearest neighbor problem in an abstract metric space," In: Pattern Recognition Letters 1:125-128.
Good et al., 1992, "Utilization of Gaussian functions for the rapid evaluation of molecular similarity," J. Chem. Inf. Comput. Sci. 32(3):188-191.
Good et al., 1992, "Similarity screening of molecular data sets," Journal of Computer-Aided Molecular Design 6:513-520.

(Continued)

*Primary Examiner* — John S Brusca
(74) *Attorney, Agent, or Firm* — VLP Law Group LLP; Richard G. A. Bone

(57) ABSTRACT

I describe several methods for organizing databases of molecular structures and searching such structures. Also described are methods for characterizing molecules based on the shapes of their fields that can be used in conjunction with the methods of organizing and searching databases. In particular, the databases of molecular structures can be analyzed by a shape metric technique, and the parameters of the decomposition can be used in creating, characterizing, and searching databases of molecules based on field similarity. The most immediate application of these techniques is to pharmaceutical drug discovery and design.

30 Claims, 9 Drawing Sheets

OTHER PUBLICATIONS

Good et al., 1995, "New molecular shape descriptors: Application in database screening," *Journal of Computer-Aided Molecular Design*, 9:1-12.

Grant et al., 1996, "A fast method of molecular shape comparison: A simple application of a Gaussian description of Molecular Shape," Journal of Computational Chemistry 17(14):1653-66.

Greene et al., 1994, "Chemical Function Queries for 3D Database Search," J. Chem. Inf. Comput. Sci. 34:1297-1308.

Grethe and Hounshell,."Similarity Searching in the development of new bioactive compounds . An application," In: Chemical Structures 2, Warr, W. A., ed., Springer-Verlag, Heidelberg. 1993. pp. 399-407.

Hahn, 1997, "Three-dimensional shape-based searching of conformationally flexible compounds," J. Chem. Inf. Comput. Sci. 37(1):80-86.

Hodgkin and Richards, 1987, "Molecular similarity based on electrostatic potential and electric field," International Journal of Quantum Chemistry: Quantum Biology Symposium 14:105-110.

Hudson et al., 1996, "Parameter based methods for compound selection from chemical databases," Quant. Struct.-Act. Relat. 15:285-289.

Jain et al., 1994, "Compass: Predicting biological activities from molecular surface properties. Performance comparisons on a steroid benchmark," Journal of Medicinal Chemistry 37(15):2315-2327.

Johnson, 1989, "A review and examination of the mathematical spaces underlying molecular similarity analysis," Journal of Mathematical Chemistry 3:117-145.

Kato et al., 1987, "A novel method for superimposing molecules and receptor mapping," Tetrahedron 43(22):5229-5236.

Martin et al., 1990, "Searching databases of three-dimensional structures," In: Reviews of Computational Chemistry, Kipkowitz, K. and Boyd, D.B., eds., vol. 1, pp. 213-263.

Mestres et al., 1997, "MIMIC: A molecular-field matching program. Exploiting applicability of molecular similarity approaches," J. Comput. Chem. 18(7):934-954.

Meyer and Richards, 1991, "Similarity of molecular shape," Journal of Computer-Aided Molecular Design 5:427-439.

Mezey, 1987, "The shape of molecular charge distributions: group theory without symmetry," Journal of Computational Chemistry 8(4):462-469.

Mezey, 1992, "Shape-similarity measures for molecular bodies: A three-dimensional topological approach to quantitative shape-activity relations," J. Chem. Inf. Comput. Sci. 32(6):650-656.

Perry and van Geerestein, 1992, "Database searching on the basis of three-dimensional molecular similarity using the SPERM program," J. Chem. Inf. Comput. Sci. 32(6):607-616.

Petitjean, 1995, "Geometric molecular similarity from volume-based distance minimization: Application to saxitoxin and tetrodotoxin," Journal of Computational Chemistry 16(1):80-90.

Petitjean, 1996, "Three-dimensional pattern recognition from molecular distance minimization," J. Chem. Inf. Comput. Sci. 36(5):1038-1049.

Petke, 1993, "Cumulative and discrete similarity analysis of electrostatic potentials and fields," Journal of Computational Chemistry 14(8):928-933.

Reynolds et al., 1998, "Lead discovery using stochastic cluster analysis (SCA): A new method for clustering structurally similar compounds," J. Chem. Inf. Comput. Sci. 38(2):305-312.

Richard, 1991, "Quantitative comparison of molecular electrostatic potentials for structure-activity studies," Journal of Computational Chemistry 12(8):959-969.

Sprague and Hoffman, "CATALYST Pharmacophore models and their utility as queries for searching 3D databases," In: Computer Assisted Lead Finding and Optimization: Current Tools for Medicinal Chemistry, Van de Waterbeemd, H., Testa, B., Folkers, G., eds., VCHA-Basel, 1997, pp. 223-240.

Thorner et al., 1997, "Similarity searching in files of three-dimensional chemical structures: Representation and searching of molecular electrostatic potentials using field-graphs," Journal of Computer-Aided Molecular Design 11:163-174.

Uhlmann, 1991, "Satisfying general proximity/similarity queries with metric trees," In: Information Processing Letters 40(4):175-179.

Walker et al., 1993, "Shape groups of the electronic isodensity surfaces for small molecules: shapes of 10-electron hydrides," Journal of Computational Chemistry 14(10):1172-1183.

Weiser et al., 1999, "Optimization of Gaussian surface calculations and extension to solvent-accesible surface areas," Journal of Computational Chemistry 20(7):688-703.

R. Pearlman, et al., "Novel Software Tools for Chemical Diversity," *Perspectives in Drug Discovery and Design*, vol. 9-11, Jan. 1998, pp. 339-353.

Supplementary European Partial Search Report dated Sep. 14, 2005 (4 pages).

Jeffrey M. Blaney and J. Scott Dixon, "Distance Geometry in Molecular Modeling", *Reviews in Computational Chemistry*, vol. 5, VCH Publishers, Inc. New York, 1994.

Perelson, A.S. et al., "Theoretical Studies of Clonal Selection: Minimal Antibody Repertoire Size and Reliability of Self-Non-self Discrimination", *Journal of Theoretical Biology*, vol. 81, No. 4 (1979), pp. 645-670.

Navasivayam, et al., "Statistical method for surface pattern-matching between dissimilar molecules: electrostatic potentials and accessible surfaces", J. Molec. Graphics, vol. 4(1), pp. 46-50 (Mar. 1986).

\* cited by examiner

METHOD AND APPARATUS FOR SEARCHING MOLECULAR STRUCTURE DATABASES

This application is a divisional application of U.S. patent application Ser. No. 09/644,937, filed Aug. 23, 2000, which itself is a continuation of international application PCT/US99/04343, filed Feb. 26, 1999, which itself claims priority under 35 USC §119(e) to U.S. provisional application Ser. No. 60/076,077 filed Feb. 26, 1998, the entire contents of all of which are incorporated by reference herein in their entirety.

FIELD OF THE INVENTION

This invention relates to methods for organizing and searching mathematical representations of molecular structures stored in a computer database. The methods are especially useful for comparing individual molecules against a large library of molecules and have particular application in the pharmaceutical industry in drug development.

BACKGROUND OF THE INVENTION

A molecule is normally thought of as a set of atoms of varying atomic type, with a certain bonding pattern. Indeed this "chemical" description can uniquely describe the molecule. It is the language that chemists use to compare and contrast different molecules. Efficient database models have been constructed to store such information for fast retrieval and storage. However, this form of description does not actually describe the three dimensional structure of the molecule, e.g., the positions of each atom, and since the interaction of molecules is a spatial event, the "chemical" description is incomplete for physical phenomena. One such phenomenon of commercial importance is the binding of drug molecules to sites of biological importance, such as the active areas or "sites" on protein surfaces, which is the mode of action of nearly all pharmaceuticals.

Drug molecules are often small, on the order of 20 atoms (excluding hydrogens). They interact with large macromolecules such as proteins by binding to them. Through binding, the drug may activate or inhibit the normal action of the macromolecule. The binding occurs at specific sites on the macromolecule, and the basis of tight and specific binding is complementarity in shape and other properties, such as electrostatic, between the two molecules.

Pharmaceutical companies maintain computer databases of all molecules they have synthesized, plus other compounds available on the market. The use of these databases and the techniques of computer-aided drug design are beginning to replace trial and error lab testing in new drug development. Important components of this process are finding new small molecules similar in shape to ones known to bind a target, and designing new molecules to fit into known or hypothesized binding sites.

There have been many attempts to describe or "encode" the three dimensional information of molecules beyond a simple list of coordinates. Many involve the distances between pairs of atoms in a molecule, i.e., an atomistic approach akin to the chemical description but with extra, spatial degrees of freedom.

A more radical departure is to adopt an alternate representation of a molecule: the field representation. A field is essentially just a number assigned to every point in space. For instance, the air temperature in a room at every point in that room forms a field quantity. Molecules have one fundamental field associated with them, namely the quantum mechanical field that describes the probability of electrons and nuclei existing at each point in space. However, this field can be thought of as giving rise to other, simpler fields of more use in understanding a molecule's properties. Chief amongst these are the steric and electrostatic fields, although others are used, such as the hydrophobic and the hydrogen bond potential field. An illustration of a Gaussian representation of a steric field is shown in FIG. 1. As is customary, on each contour line in the field, each point has equal value.

Steric fields describe the mass or shape of the molecule, and at the simplest level such a field might have a value of one inside the molecule and zero outside. Electrostatic fields represent the energy it would take to place an electron at a particular place in space, by convention positive if the energy is unfavorable and negative if favorable. These two fields are the most relevant for molecular interactions because of basic physical laws, i.e., that two molecules cannot overlap (steric repulsion) and that positive atoms like to be near negative atoms and vice versa. These are the basic components of molecular interactions.

If a molecule is known to bind and have effect on some biological target, it is of great commercial interest to find other molecules of similar shape and electrostatic properties (i.e., similar fields) since this enhances the likelihood of such molecules having similar biological activity. Since shape and electrostatic character are consequences of the underlying atoms, which can be efficiently encoded by a chemical description, such searches have traditionally been performed at this level, by looking for molecules which are "chemically" similar. One disadvantage of this approach is that the relationship between chemical similarity and structural similarity is not precise; and chemically similar molecules may be structurally quite different. Another disadvantage is that a chemically similar compound may well be covered by the same patents as the original molecule. Finally, searching only chemically similar compounds inevitably means one will not find active molecules that are not chemically similar.

This latter point is key. David Weininger of Daylight Chemical Information Systems has reported an analysis that suggests there are $10^{200}$ different molecules synthesisable by known means. (Only $10^{107}$ molecules of typical drug size would fit in the known universe!). As such, any molecule, of any shape or electrostatic profile, has a potentially astronomical number of similarly shaped and charged "doppelgangers". Only a fraction of them are necessarily chemically similar. Hence by restricting the search to chemical similarity a vast number of potential drug leads are never discovered.

Although $10^{200}$ molecules is too large a number to ever enumerate, I believe that it is possible to determine bounds to the possible variations of molecular fields of this hypothetical set. Furthermore, I plan to compute for database storage a very large number of molecular structures (e.g., of the order of billions) that sample this range such that I am able to find a match, or "mimic", from this collection to any novel structure presented. Such a database would be many thousands of times larger than any currently in existence and hence crucial to this plan is the efficient organization of such for fast search and retrieval of such mimics and the assessment of whether I have indeed "covered" chemical space. It is these problems that the present invention addresses.

State Of The Art

Much has been done in the use of molecular fields to compare and contrast molecules and to predict activity from such operations. Some of these approaches are described below. I believe that the crucial aspect of my approach which differs from all prior work is in the application of a particular property of field comparison, namely the "metric" property, and in a novel way to decompose fields into separable domains, wherein each is quantifiably similar to a geometrically simpler field.

The most widely known "field analysis" approach is that known as Comparative Molecular Field Activity (COMFA). See U.S. Pat. Nos. 5,025,388 and 5,307,287 assigned to Tripos Inc. of St. Louis, Mo. The idea behind COMFA is to take a series of molecules of known activity and to find which parts of these molecules are responsible for activity. The procedure is to first overlay the set of molecules onto each other such that the combined difference of the steric and electrostatic fields between all pairs of molecules is at a minimum. (The concept of overlaying, i.e., finding an orientation between a pair of molecules that minimizes a field difference is fundamental to all methods that utilize molecular fields for molecular comparison.)

Given this ensemble average, one then finds values of properties such as the electrostatic field at a number of grid points surrounding the set of molecules. These then become data points in a statistical analysis known as Partial Least Squares (PLS), which seeks to identify which points correlate with some measure of activity. For instance, if all active molecules, once overlaid, had a similar region of positive potential, while less active or inactive molecules did not, the procedure would identify this as an important common motif in activity.

Problems inherent in COMFA are the multiple alignment of a set of molecules, the placement of grid points near the molecules, and the interpretation of the PLS output.

Another approach which uses molecular overlay is that set forth in U.S. Pat. Nos. 5,526,281 and 5,703,792 of Chapman et al. of ARRIS Inc. They are interested in selecting a subset of compounds from a much larger set that retains much of the diversity of the larger set. The basic concept is to start with as few as one molecule as the representative set, then to overlay a candidate molecule to minimize steric and/or electrostatic field differences to all in the set, and then to calculate differences between the molecules based upon this alignment. This is repeated for each of the candidate molecules. The candidate which is "most different" from those already in the representative set is added and the procedure then repeated until the number of compounds chosen reaches a desired threshold.

In both COMFA and the Chapman approach, field similarity is used as a tool to solve the alignment issue, and similarities or differences are then calculated. The value of the field similarity or difference is of secondary importance, it merely solves what is called the "assignment" problem, i.e., which atoms, or areas of a molecule's field are "equivalent".

In contrast, in Mestres et al., "A Molecular Field-Based Approach to Pharmacophoric Pattern Recognition," *J. Molecular Graphics and Modelling*, Vol. 15, pp. 114-121 (April 1997) incorporated herein by reference, molecules are aligned based upon the overlap of their steric or electrostatic fields, or by a weighted sum of the two. A similarity measure is defined that equals one when the fields are the same, and minus one when they are maximally different. The Mestres et al. work is embodied in a program called MIMIC, which performs global and local optimization of the field overlap. They note that there are several possible overlays that have the appearance of being the best overlap. These are so called "local minima", because while small displacements lead to a decrease in their similarity function, they may not be the best "global" solution. This is as expected since field overlay belongs to the class of problems known to have "multiple minima". Mathematically this is usually an intractable problem, solvable only by much computation, e.g., as is evident in the descriptions by Mestres et al. In fact, the multiple overlay solutions are one of the key aspects of their work, in that one cannot be sure which is the most "biologically" relevant overlay, and what might be the correct weighting of steric to electrostatic fields.

An additional aspect considered by Mestres et al. is the issue of molecules existing in multiple structural conformations, i.e., energetically there may be more than one possible structure for a given molecule. Mestres et al. calculate the similarity indexes of all pairs of conformations of a molecule and perform what is known as principal component analysis (PCA). They do this to find representatives of all possible conformations that are most distinct. Although this procedure is really akin to finding the dimensionality of the space in which these conformers exist, Mestres et al. do not use PCA for this purpose, but merely to cluster the conformers. They do not apply PCA to sets of different molecules, only to conformers of the same molecule, and they do not use any other "metric" property of their similarity measure. In fact they seem unaware of such.

There is an important distinction to be made between a "measure" of similarity and a "metric" of similarity, although these words are often used interchangeably. A measure can be any quantity which has a correspondence with molecular similarity, i.e., the idea that the more similar the measure the more similar the compounds. A metric has a precise mathematical interpretation, namely that if the metric, or more commonly the metric distance, between A and B is zero then the two items are the same item, that the distance from A to B is the same as the distance from B to A, and that the distance from A to B plus the distance from B to a third compound C must be greater than the distance from A to C. This latter is called the "Triangle Inequality" because the same conditions can be said of the sides of a triangle ABC. The Triangle Inequality, or metric upper bound, also leads to a lower bound, namely that in the case above, C can be no closer to A than the difference of these distances A to B and B to C.

In M. Petitjean, "Geometric Molecular Similarity from Volume-Based Distance Minimization-Application to Saxitoxin and Tetrodotoxin," *J. Computational Chemistry*, Vol. 16, No. 1, pp. 80-95 (1995) incorporated herein by reference, it is recognized that the quantity that measures the overlay of fields forms a metric quantity, and that the measure of the optimum overlay of two fields also forms a metric which is intrinsic to the molecule, i.e., independent of orientation or position.

A metric distance may also be used in a technique called "embedding". The number of links between the elements of a set of N elements can be shown to be $N*(N-1)/2$ and each link can be shown to be a metric distance. While a set of N elements has $N*(N-1)/2$ distances, the set can always be represented by an ordered set of $(N-1)$ numbers, i.e., I can "embed" from a set of distances to a set of N positions in $(N-1)$ dimensional space. This is identical to Principal Component Analysis mentioned previously, except that with PCA one finds the most "important" dimensions, i.e., the "principal" directions, which carry most of the variation in position. Typically with PCA one truncates the dimensionality at 2 or 3 for graphical display purposes. In general, the number of dimensions which reproduces the set of $N*(N-1)/2$ distances within an acceptable tolerance may be much smaller than $(N-1)$, yet still be greater than 2 or 3. Hence one talks of "embedding into a hyper-dimensional subspace", where hyper-dimensional means more than 3 dimensions, and subspace means less than $(N-1)$. Techniques for such an embedding are standard linear algebra. When applied to molecular fields, the result of embedding is a shape-space of $M \leq N-1$ dimensions.

SUMMARY OF THE INVENTION

I have invented several techniques for characterizing molecules based on the shapes of their fields. The minimal distance between two molecular fields is used as a shape-based metric, independent of the underlying chemical structure, and a high-dimensional shape space description of the molecules is generated. These attributes can be used in creating, characterizing, and searching databases of molecules based on field similarity. In particular, they allow searches of a database in sublinear time. The utility of this approach can be extended to automatically break molecules into a series of fragments by using an ellipsoidal Gaussian decomposition. Not only can these fragments then be analyzed by the shape metric technique described above, but the parameters of the decomposition themselves can also be used to further organize and search databases. The ellipsoidal method can also be used to describe binding or active sites on macromolecules, providing a template for searching for complementary molecules in a database such as I describe. The most immediate application of these techniques is to pharmaceutical drug discovery and design.

In a preferred embodiment, I obtain the minimal distance between a first molecular field and a multiplicity N of other fields by: selecting a small number M of the fields, for each of the M fields determining its metric distance to all the other N fields, for each of the M fields, making an ordered list of the metric distances between that field and all the other N fields, determining the metric distances between the first field and each of the M fields, determining the metric distances between the first field and the fields on the ordered list associated with the M field that has the shortest metric distance between it and the first field. These metric distances are determined beginning with the field on the list that has the shortest metric distance between it and the M field and continuing such determination with fields having increasingly greater metric distances from the M field until a field is reached that has a metric distance from the M field that is more than twice the metric distance from the first field to the M field.

Advantageously, the invention is practiced on a computer, the determination of minimal distances and ellipsoidal Gaussian decomposition are implemented by computer programs and the molecular field information is stored in a computer database. Illustrative apparatus for practicing the invention is a personal computer such as an IBM-compatible PC or a work station such as a Silicon Graphics Iris Indigo Elan 4000.

BRIEF DESCRIPTION OF THE DRAWINGS

These and other objects, features and advantages of my invention will be more readily apparent from the following detailed description of the invention in which.

DETAILED DESCRIPTION OF THE INVENTION

Definitions

Figure 1:
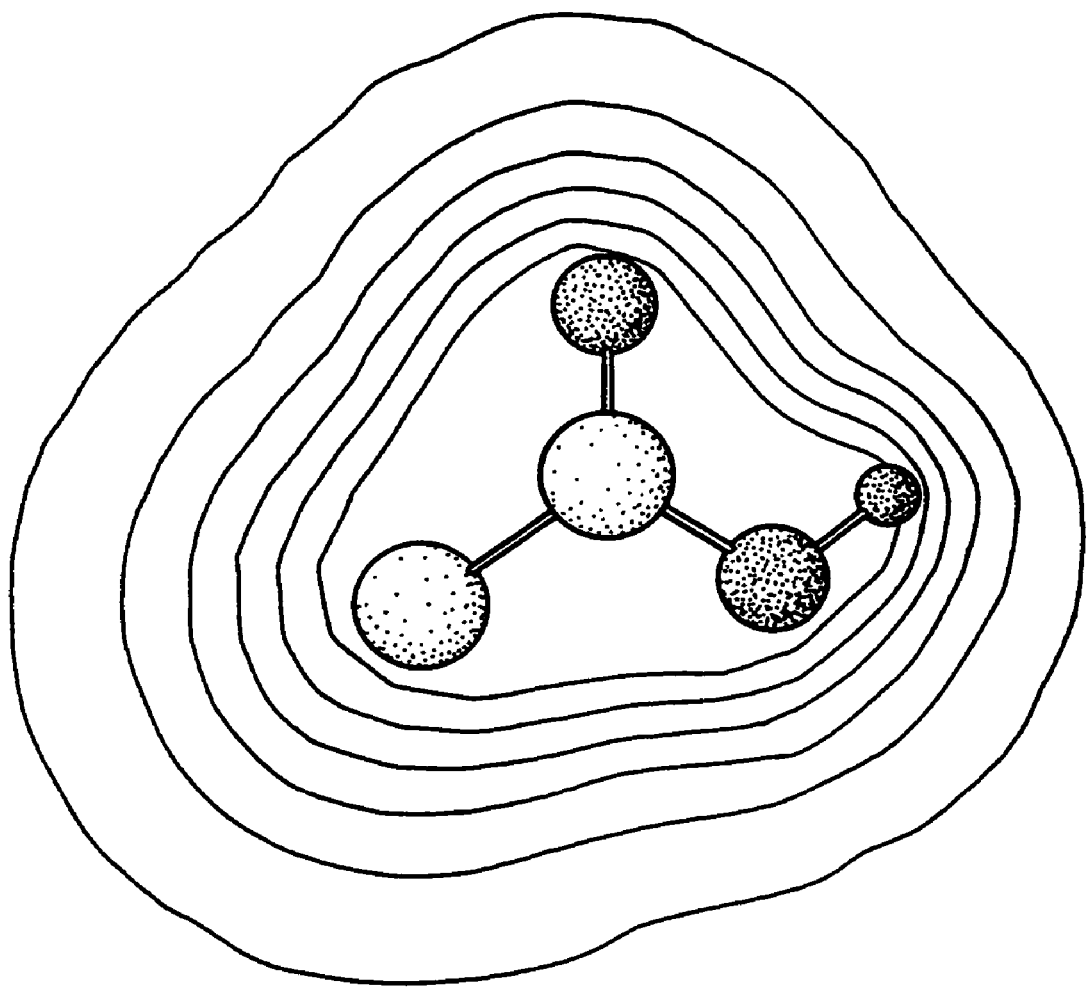
FIG. 1 is an illustration of a Gaussian representation of a steric field.

The following defined terms are used in the detailed description:

A "structure": A description of the three dimensional coordinates of each of the atoms that comprise a molecule. These coordinates may be found from experiment, e.g., X-ray crystallography, or by computer computation by one of many methods known in the field of molecular modeling.

A "conformer": If a molecule has more than one structure, then each structure is referred to as a conformer of that molecule.

A "molecular field", or "field": A set of numbers that represent the value of some property in and around a molecule. Such numbers may be explicitly stated, or listed, for instance as values associated with each point on a regular lattice, or grid, which contains the molecule. Or they may be functionally implied. For instance, if a functional form for the field property is assigned to each atom then a mechanism exists to calculate the field value at any point in space. One example is the electrostatic potential around a molecule, one form of which may be calculated from the charge associated at each atom and the functional form for electrostatic potential from a single charge, i.e., Coulomb's Law.

A "Gaussian molecular field": A particular instance of a functionally implied molecular field with which I am much concerned is that produced by assigning a Gaussian function to each atom to represent the steric field of that molecule. A Gaussian function is one that has the form:

$$G_i(\vec{r}) = p_i e^{-w_i((x-a_i)^2 + (y-b_i)^2 + (z-c_i)^2)} \quad (1)$$

where the position vector is $$\vec{r} = (x, y, z)$$

and where for any atom i, $p_i$ is a prefactor, $w_i$ is a width factor, $a_i$, $b_i$, and $c_i$ are the Cartesian coordinates of the atom center, and $x_i$, $y_i$, and $z_i$ are the Cartesian coordinates of any point in space.

"Sum" and "Product forms" of Gaussian fields: Upon assignment of prefactors and widths to the Gaussian associated with each atom there are many ways of generating a steric field, but the two that will be referred to in this description are the sum and product forms.

Sum Form:

$$F_M(\vec{r}) = \sum_{i=1}^{N} G_i(\vec{r}) \quad (2)$$

Exclusion Product Form:

$$F_M(\vec{r}) = 1 - \prod_{i=1}^{N} (1 - G_i(\vec{r})) \quad (3)$$

where $F_M$ is the steric field of a molecule with structure and orientation M made up of N atoms represented by Gaussian functions $G_i$ centered about each atom i. Each form has the property of having zero values away from the molecule and usually positive values "inside" the molecule. The exclusion product form expands to a sum of Gaussians, because the product of two Gaussians is itself a Gaussian function.

"Field Arithmetic": Two fields are added together by adding their values at corresponding grid points, or by adding together the functional forms that define the field. A field can be "scaled" by multiplying either the value at each grid point, or the functional form, by a number. Two fields can by multiplied together by multiplying the values at corresponding grid points by each other or multiplying their functional forms together.

"Field Volume": For any field function $F_M$ the field volume is given by its integral over all space $$V = \int F_M(\bar{r}) dV \tag{4}$$

or if the field is represented for example on a three dimensional grid with sides of I, J, and K points, $$V = \sum_{i=1}^{I} \sum_{j=1}^{J} \sum_{k=1}^{K} F_{M_{i,j,k}} \cdot v_{i,j,k} \tag{5}$$

where $F_{M_{i,j,k}}$ is the value associated with grid point i,j,k and $v_{i,j,k}$ is the volume associated with that grid point. On a regular grid $v_{i,j,k}$ would be a constant.

The overlap Q of two fields $F_M$ and $F_P$ is given by $$Q = \int F_M(\bar{r}) F_P(\bar{r}) d\bar{r} \tag{6}$$

for a continuous case, or $$Q = \sum_{i=1}^{I} \sum_{j=1}^{J} \sum_{k=1}^{K} F_{M_{i,j,k}} F_{P_{i,j,k}} v_{i,j,k} \tag{7}$$

if the molecule is represented on a grid as described above in Field Volume.

The "norm" of a field $F_M$ is defined as the square root of the overlap of that field with itself, i.e., $$|F_M| = \sqrt{\int F_M(\bar{r}) F_M(\bar{r}) d\bar{r}} \tag{8}$$

The "norm of the field difference", also referred to as the "field difference" D, is given by $$D = |F_M - F_P| = \sqrt{\int (F_M(\bar{r}) - F_P(\bar{r}))^2 d\bar{r}} \tag{9}$$

The greater the field overlap, the less the field difference, as can be shown by rewriting the above equation as $$D^2 = \int F_M^2(\bar{r}) d\bar{r} + \int F_P^2(\bar{r}) d\bar{r} - 2 \int F_M(\bar{r}) F_P(\bar{r}) d\bar{r} \tag{10}$$

Only the third integral varies if $F_M$ and $F_P$ are moved relative to each other. But this third integral is equal to the overlap $Q_{MP}$. Thus the larger the overlap, the smaller is $D^2$, and hence the smaller the field difference D.

The "metric triangle inequality": If the distance $d_{AB}$ from A to B is known, and the distance $d_{BC}$ from B to C is known, the triangle inequality states that for the distance $d_{AC}$:

$$d_{AC} \leq d_{AB} + d_{BC} \tag{11}$$

and from this it also follows that $$|d_{AB} - d_{BC}| \leq d_{AC} \tag{12}$$

These are the upper and lower bounds, respectively, for the value of $d_{AC}$.

Ellipsoidal Gaussian Function (EGF)

The overlay of molecular fields is a method of finding global similarities between molecules, i.e., whether molecule A has the same distribution of properties as molecule B. While this is extremely useful, it is also the case that local similarities are of interest, i.e., when a part of molecule A is similar to a part or all of molecule B. The methods described below are an approach to solve this problem by defining representations of parts of a molecular field which have an approximately ellipsoidal character. These representations conform to visual and chemical intuition as to possible fragmentations of a molecular structure, and can be compared between molecules either singly or in combination with ease.

An EGF for a molecule M is defined as:

$$EGF_{M,i}(\bar{r}) = p_i e^{u_i (\bar{d}_i \cdot \bar{A}_i)^2 - v_i (\bar{d}_i \cdot \bar{B}_i)^2 - w_i (\bar{d}_i \cdot \bar{C}_i)^2} \tag{13}$$

for the $i^{th}$ of K ellipsoidal Gaussian functions fit to some molecular field $F_M(r)$, where K may be as small as 1, and where the displacement vector is $$\bar{d}_i = (x - a_i, y - b_i, z - c_i)$$

and the position vector $$\bar{r} = (x, y, z)$$

and where $p_i$ is a prefactor, $u_i$, $v_i$ and $w_i$ are width factors, $a_i$, $b_i$ and $c_i$ are the coordinates of the center of the EGF, and $x_i$, $y_i$, and $z_i$ are the coordinates of any point in space. $A_i$, $B_i$, and $C_i$ are three mutually orthogonal unit vectors that define the directions of the ellipsoidal axes.

An Ellipsoidal Gaussian Representation (EGR) of a molecular structure is constructed by fitting one or more Ellipsoidal Gaussian Functions (EGF) to a field function of a molecule, for instance a steric or electrostatic field.

The "EGR field" is defined as the sum or exclusion product of the fields generated by the EGF's. For the EGR of a molecular field decomposed into N EGF fragments:

Sum Form:

$$EGR_M(\bar{r}) = \sum_{i=1}^{N} EGF_{M,i}(\bar{r}) \tag{14}$$

Exclusion Product Form:

$$EGR_M(\bar{r}) = 1 - \prod_{i=1}^{N} (1 - EGF_{M,i}(\bar{r})) \tag{15}$$

The Sum Form of the EGR is currently preferred.

The procedure for fitting one or more EGF's to a molecular field involves ascertaining the parameters of each EGF, i.e., center (a,b,c), widths (u,v,w), and axes directions (A,B,C) that minimize the integral over all space of the square of the field difference between the molecular field and the EGF field. This integral is referred to as the EGR Fitness Function (EFF).

$$EFF(EGR_M, F_M) = \int (EGR_M(\bar{r}) - F_M(\bar{r}))^2 d\bar{r}$$

Overview

To compare two molecules A and B, I determine the difference between their fields A and B using the norm of the field difference shown in equation (9). The norm of the field difference constitutes a metric distance, not just a similarity measure. Furthermore, the minimal value of d, $d_m$, which occurs at the point of maximal overlap of the two, also forms a metric.

Figure 2B:
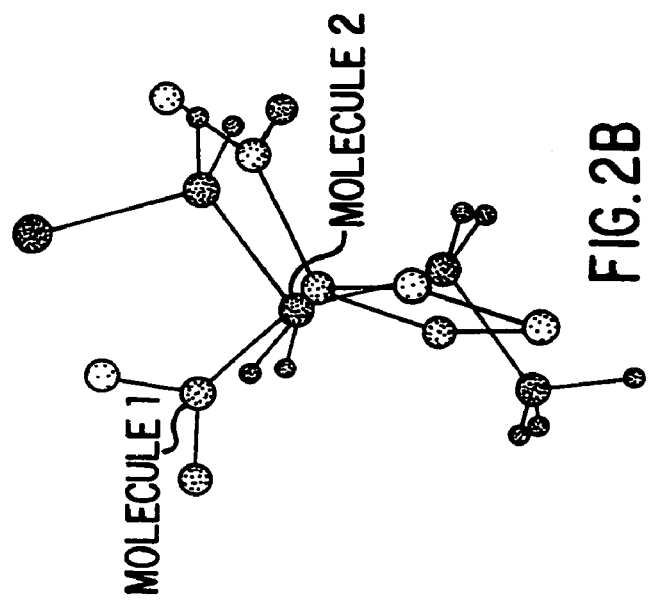
FIGS. 2A and 2B illustrate the results of overlaying two molecules using a prior art technique.
Figure 2A:
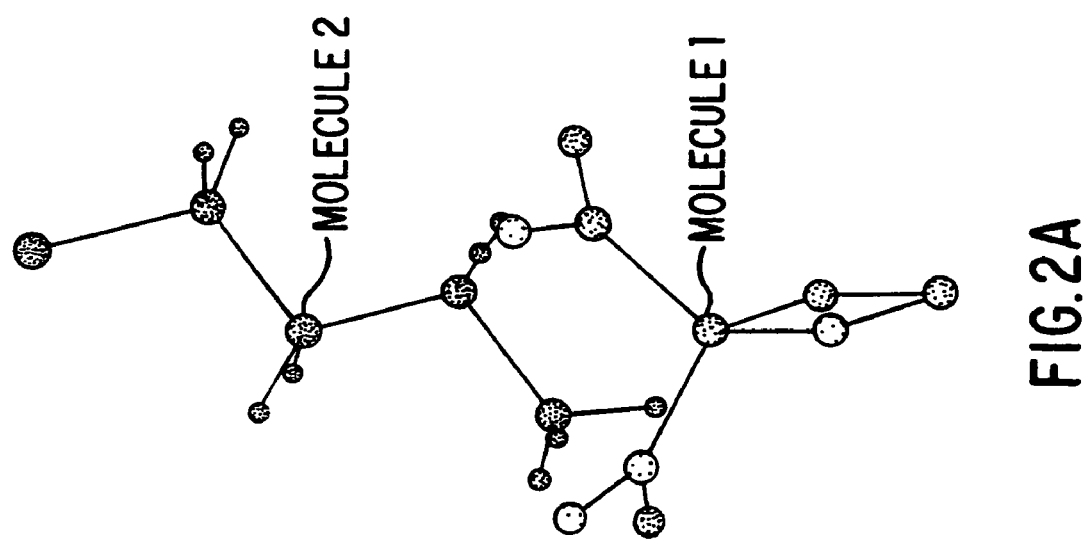

Various techniques exist to attempt to find the best overlap of two fields, typically involving repeated searches from different starting orientations of the two molecules. This is necessary because no direct solution for the minimal distance orientation is available, and most methods tend to get caught in nearby local minima, missing the global minimum. One such technique is a Gaussian technique described in J. A. Grant et al., "A Fast Method of Molecular Shape Comparison: A Simple Application of a Gaussian Description of Molecular Shape," *J. Computational Chemistry*, Vol. 17, No. 14, pp. 1653-66 (1996), incorporated herein by reference. Using this technique, I overlaid the two molecules shown in FIG. 2A to produce the result shown in FIG. 2B.

This Gaussian technique is less susceptible than other techniques to being caught in local minima. Because $d_m$, once found, is an invariant, fundamental distance between the two molecular fields, it can be used in creating a hyper-dimensional embedding of a set of molecules. This hyper-dimensional space is called a "shape space", (but where "shape" can mean electrostatics or other field properties, not just steric fields). I believe that for small molecules the number of dimensions will be on the order of a few dozen.

In the following, I may refer interchangeably to maximal overlap (or overlay), minimal field difference, and minimal distance, as they all refer to and measure the same optimal orientation of two molecules with respect to each other.

Rather than merely use the overlay optimization as a method of aligning molecules for further similarity comparison, I use the overlay measure as a metric distance for the organization of large numbers of structures such that searches within this dataset can be made "efficient". Efficiency here can be precisely defined in the language of database algorithms: the search time can be made "sublinear", i.e., one does not have to check every entry (a "linear" search). A large body of literature deals with algorithms for sublinear searching when a metric exists to pre-organize a database of knowledge. I have not decided upon an optimum approach as yet because there are still many aspects not explored which can impact efficiency, i.e., the nature of the shape space molecular fields occupy. Basic "vanilla" database approaches ignore such and merely use the distances between data entries to organize the data, whereas more sophisticated approaches utilize shape space characteristics.

In all of my methods for using the field metric, the steric field for each molecule is constructed either from a sum of Gaussians centered at each atom, or as one minus the product of one minus each such Gaussian. These are referred to as the "sum form" and "product form" respectively. The product form has the advantage that it removes excess internal overlap and hence is smoother inside. The sum form has the advantage that it is numerically simpler. Each Gaussian is such that its volume is the same as that of the atom it represents, and the volume, as of any field, is calculated from the integral of the function over all space.

A simple use of the metric property is to speed the search for the best global overlay (minimum field difference or distance) between two molecules. Consider the situation where the difference measure is calculated for molecule A and molecule B in one orientation, and I want to know the difference measure for molecule A and B where B has been placed in a different orientation. I am free to think of this second instance of molecule B as a different molecule C. If I know the difference between B and second B (C) then I have a measure, via the triangle inequality, of the maximum and minimum values of the difference between A and this other B. See equations (11) and (12).

Both upper and lower metric bounds are very useful in database searching when large numbers of data items must be compared. For instance, suppose one is looking for the closest item in the database to a given query example (A) and the metric distance between this example and one particular member (B) of the database is small, say D. If one has pre-calculated and stored the distances between all pairs of data entries in the database, then there is no need to search any entry (C) which has a distance of more than 2D from the particular member (B) because the metric lower bound specifies any such entry must be more dissimilar.

If the lower bound to d(AC) is still too large to be considered for further study I can eliminate entry (C) from further consideration as a global minimum. Hence, if I know d(BC) I can "prune" my search space for the best overlay. But since d(BC) merely involves the overlap of B with itself in a different orientation, these values can be pre-calculated, stored along with other quantities associated with B, and used to speed the search for the best overlay of B with A or any other molecule.

Finding the shape space position of a molecule not part of the original shape space characterization is done by a high-dimensional equivalent of triangulation, i.e., given a dimensionality of N I need the distance of the molecule to at most N+1 other molecules which have already had their shape space vectors calculated. This is again standard linear algebra.

The positions in shape space can also be used as characteristics in other procedures, for instance in a Partial Least Squares analysis to find the components that correlate with activity. Shape space positions can also be used to assess the diversity of a set of compounds, i.e., are they spread evenly or clustered within the shape space defined by their mutual distance. Various statistical measures can be applied to this set of positions, e.g., finding the degree of clustering, the largest "gap" or void in the shape space so defined etc. Another use is to compare two sets of compounds which have both had shape space characterization, i.e., are there parts of shape space in one set not covered in the second and vice versa; what molecules can be omitted in a merged set based upon shape similarity; which compounds fill the largest void in the other set's shape space, etc. Finally, given a large database whose dimensionality has been determined, one could find a smaller representative set of molecules that retain the same dimensionality, i.e., the same diversity.

These positions can also be used to guide the layout of the data within a database for efficient search and retrieval by standard methods. For instance, a method known as N-dimensional trees orders data by each dimension in turn and can reduce the search time for finding all entries within a certain distance of a query to a constant multiplied by the logarithm of the number of entries in the database. For instance, if there are 1,000,000 entries one only has to check of order 6*constant entries, and for 10,000,000 only 7*constant entries. Another method is known as "Vantage Trees", wherein the data is organized about certain "vantage" points, for instance the center of clusters of molecules in shape space. A third method chooses a set of key compounds, and for each of these, lists all the molecules in order of distance from it.

For example, if I have 1,000 molecules in my database I might organize this information thus: select 10 "key" molecules which are quite different in shape. For each of these 10 key molecules I then find the distance from each of these molecules to every other molecule in the database, and make 10 lists where each list has a different key molecule at the top and the rest of the 999 molecules are listed in order of shortest distance from it. To find the closest match between a test molecule and the 1,000 molecules of the database I begin by determining the metric distances between the test molecule and each of the key molecules. Suppose the shortest distance is to key molecule 6 and that distance is X. I now begin to calculate the distances to the rest of the molecules, but in the order specified by that key molecule's list. Since the list has molecules close to key molecule 6 first, it is likely these are also close to my test molecule. Furthermore, by the triangle inequality, since molecules which are a distance greater than 2× from key molecule 6 must be greater than X from my test molecule, I only have to go down the list until this condition is satisfied, i.e., I may not have to test all 1,000 molecules. Furthermore, if I find a molecule closer than key molecule 6 early in the list, say distance X−d, then I only have to go down the list until the distance from the key molecule is greater than 2(X−d), i.e., I can refine the cutoff distance as I progress down the list. Thus I can search the database, by shape, in a time sublinear with the number of molecules in the database. These methods are not possible without evaluating a shape space description of the set of molecules that comprise the database.

Ultimately 1 hope to characterize the shape space of all synthesizable molecules, i.e., the $10^{200}$ referred to earlier. But the shape space of smaller sets of molecules can be determined as well. The "position" of a molecule in such a high dimensional shape space then allows one to calculate the best possible overlay between two molecules without any computer intensive minimization of the overlap of two fields, or searching through multiple minima. (The distance between these two points is just the square root of the sum of the squares of the values assigned to each coordinate in shape space, i.e., a higher order generalization of finding the distance between any two points in three-dimensional space.) I anticipate this will provide nearly a thousand-fold speedup in the calculation of the best overlap between two molecules, if their shape space positions are known, relative to my current best methods (which are already hundreds of times faster than any reported in the literature).

The field similarity methods I have described apply to the total field that represents a molecule, and as such is a measure of "global" similarity. Yet, very often in searching for similar molecules one is satisfied with a match to parts of a molecule, i.e., either all of molecule A matching part of molecule B, or a part of A matching a part or all of B. The reason this "subdomain" or "local" match problem is important is that not all of a molecule's mass may be involved in its biological function.

The intrinsic problem in subdomain matching is deciding how to break up a molecule into smaller fragments. Very quickly the problem can generate combinatorially large numbers of sub-molecules. When there are good methods available to avoid this explosion in the number of fragments (for instance, when a molecule is synthesized from a collection of smaller subfragments) then each fragment may be analyzed by the same "global" methods described in previous sections. In general though, this "submolecule" matching is a graph theoretic problem upon which many lifetimes of scholarly energy have been expended.

My approach is simple and yet quite powerful. I seek to represent the molecular field by certain simpler shapes, namely ellipsoidal Gaussian functions (EGF). An EGF is a mathematical form that specifies a value at each point in space that is equal to:

$$p^*\exp(-ax^2-by^2-cz^2)$$

where x, y and z are distances in mutually orthogonal directions from a particular point in space, a, b and c are positive constants, and p may be positive or negative but is usually positive. This function falls off rapidly far from its center and has the symmetry of an ellipsoid.

Figure 3:
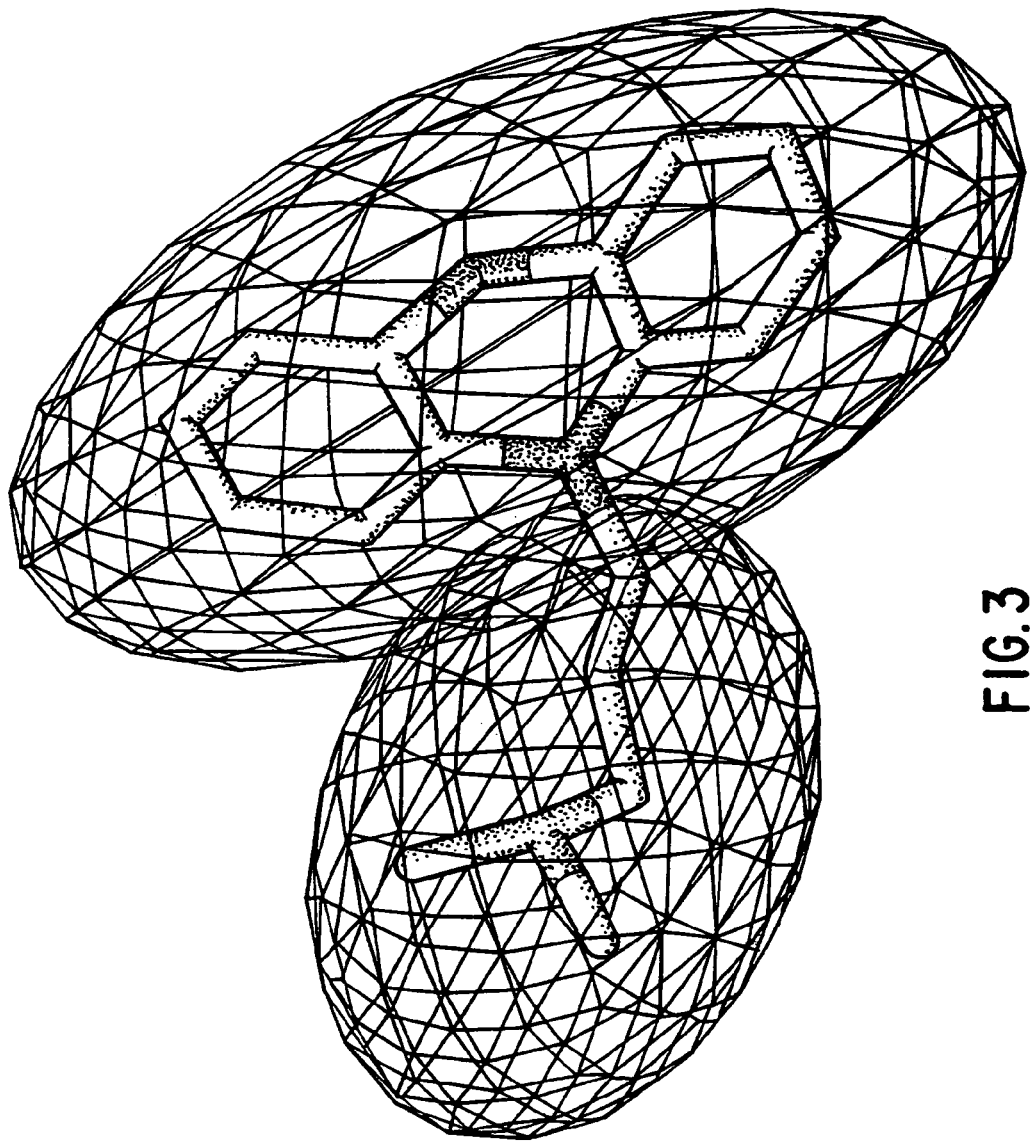
FIG. 3 is an illustration of a molecular field representation produced in accordance with the invention.

The procedure is as follows:
a) Choose the number of EGF's that I want to represent the field.
b) Choose random positions for the center of each EGF and make each spherical, i.e., $a=b=c=1$.
c) Let the center, directions and magnitudes of each EGF change such as to maximize the field overlap between this set and the molecular field. Many standard numerical techniques, e.g., steepest descent, conjugate gradient method, can perform this minimization. I have encoded the first and second derivatives of this overlap function, which leads to particularly efficient minimizations. An example of the EGF produced by this method is shown in FIG. 3.

Figure 4A:
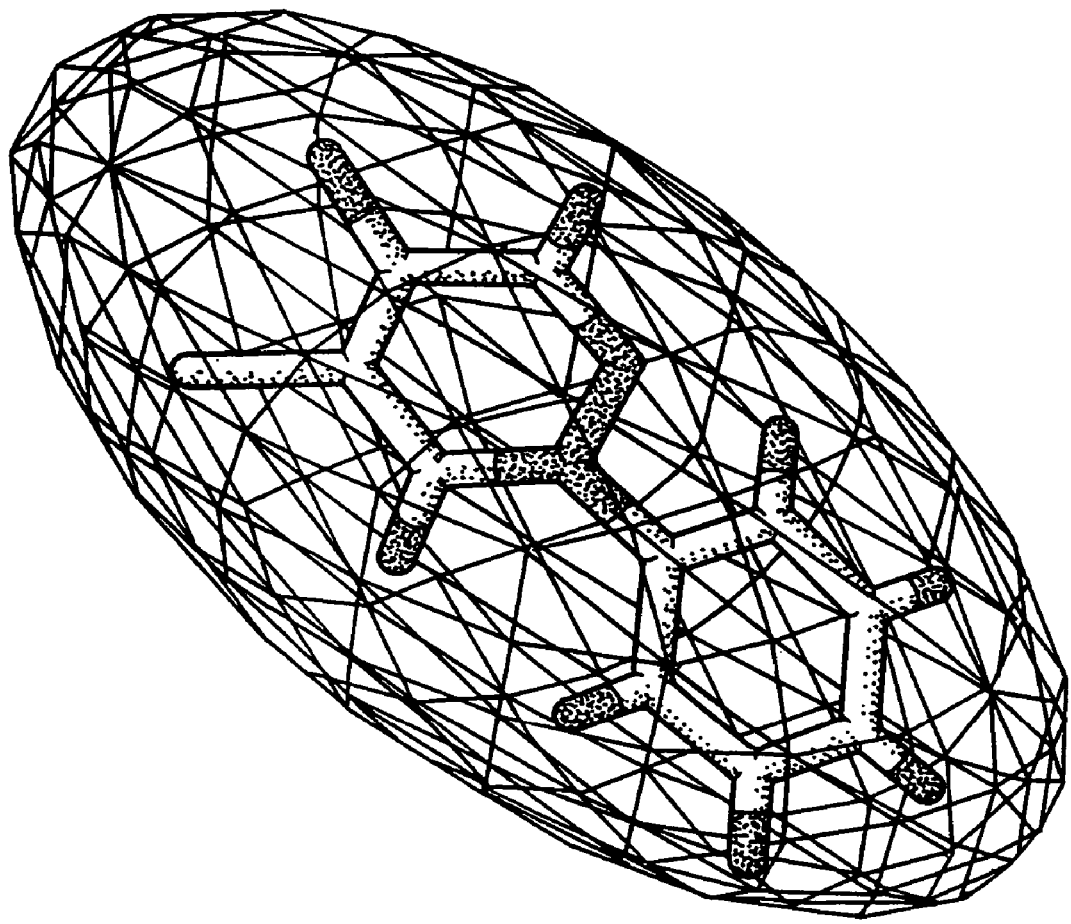
FIGS. 4A, 4B and 4C are examples of three molecular field representations formed using increasing numbers of ellipsoidal Gaussian functions in accordance with the invention.
Figure 4B:
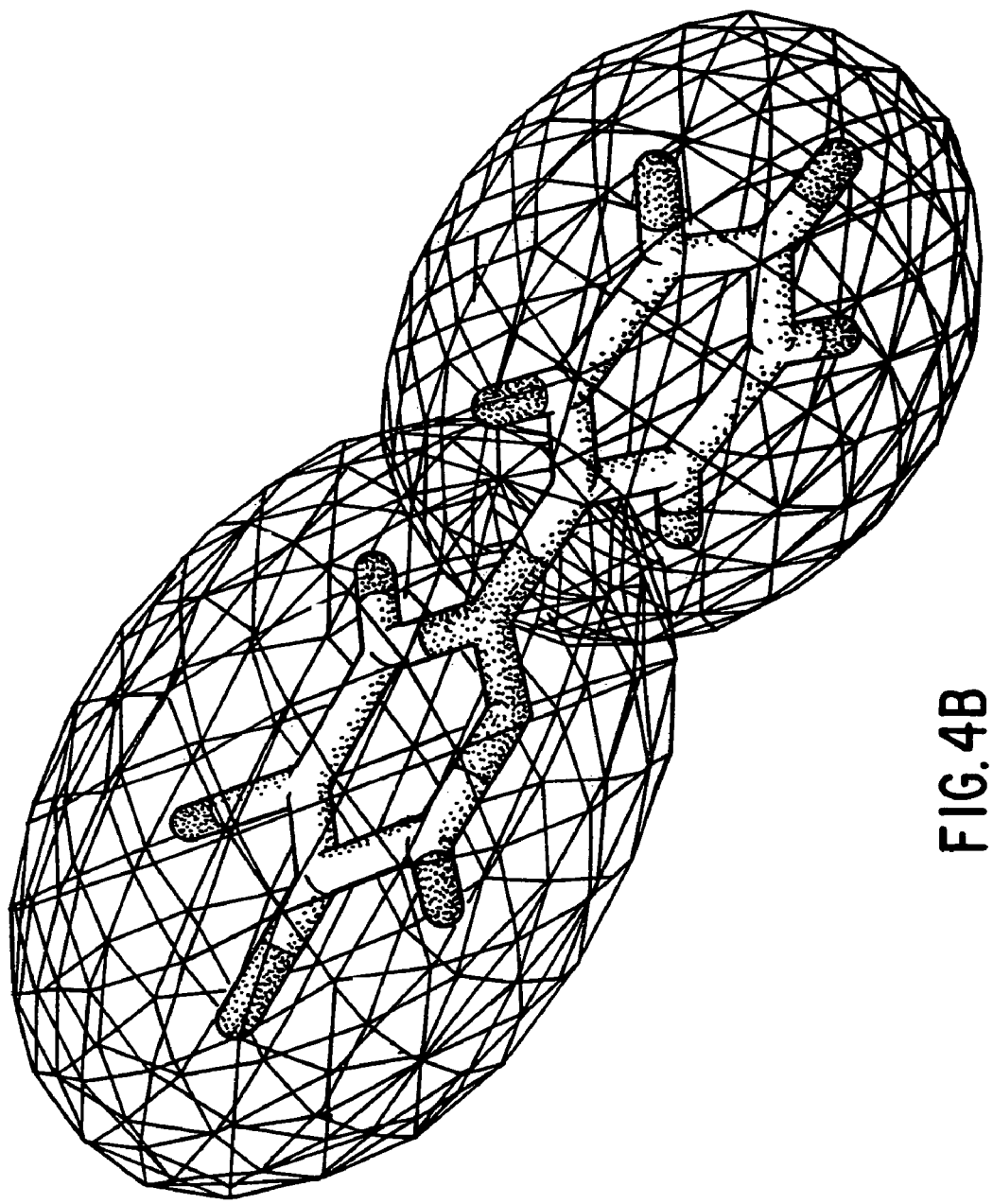
Figure 4C:
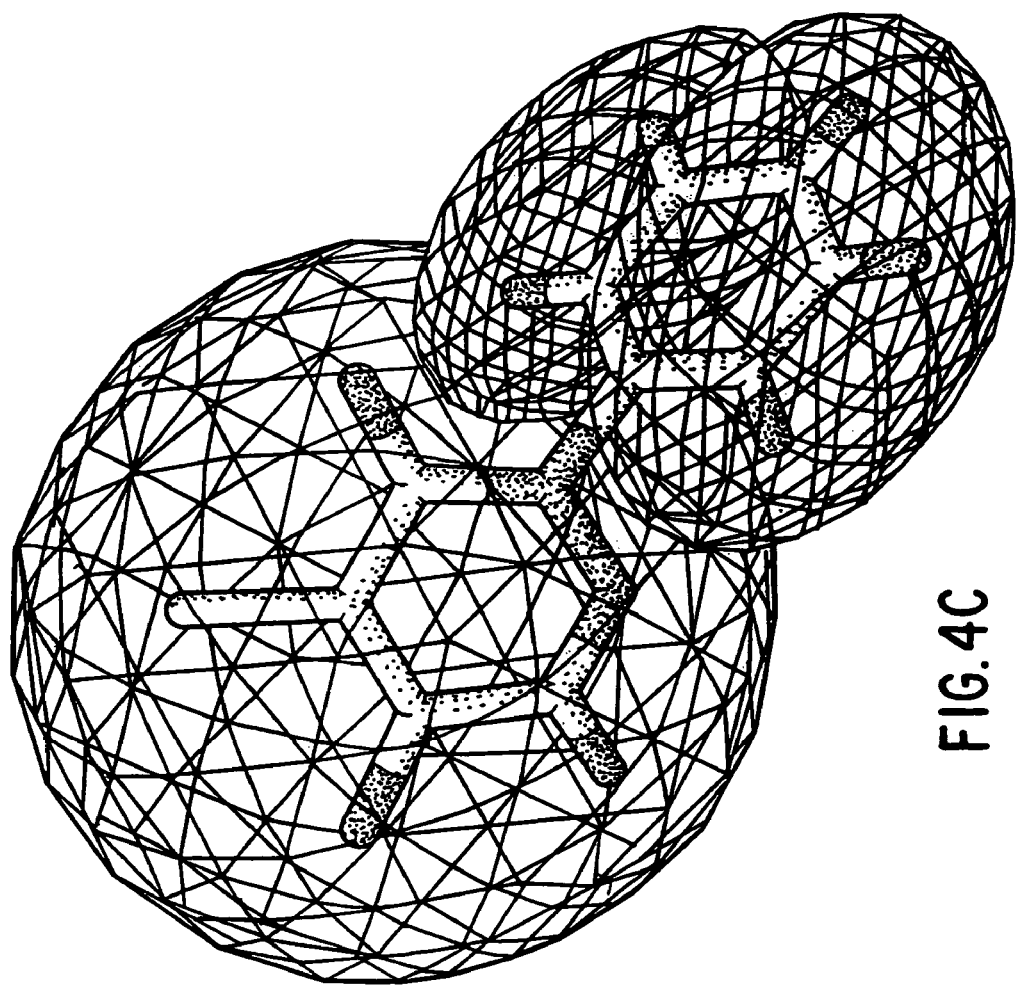

The above is also a multiple minima problem, and once this procedure has been completed one typically repeats it with new starting positions, i.e., there is more than one possible representation of a molecular field by a set of EGF's. One also tries increasing numbers of EGF's, i.e., one, then two, then three, etc., as illustrated by FIGS. 4A, 4B and 4C. Small drug-like molecules typically require at most 3 or 4 ellipsoids to represent them well. I can construct a measure of how many EGF's are needed by also measuring the field overlap of each EGF with the atoms that lie within its domain, where each such atom is represented as a spherical Gaussian. This value of fit typically gets worse as the overall fit gets better (i.e., as the fit gets tighter, atoms may be split across EGF boundaries) and hence the sum of the two is a quantity which first increases with number of EGF's but then decreases, the maximal value indicating the "best" number of EGF's for that molecule, although I also keep "sub-optimal" representations since these may also be useful.

One can now use the EGF's in the molecular comparison problem in numerous ways. For instance, the simplest is to deconstruct the molecule into separate sets of atoms, each of which is then operated upon by my shape space methods, i.e., as an automatic, non-chemistry based method of fragment construction.

One can also use the EGF decomposition to organize the storage of molecular shape information. For instance the volumes and orientations of each EGF can be used as keys in an index for rapidly finding similarly decomposed molecules. Because the actual number of EGF's in any representation is small, e.g., 3 or 4, one can also store all subsets of EGF's. For instance a four EGF set ABCD could be stored on the basis of ABCD, ABC, ABD, ACD, BCD, AB, AC, AD, BC, BD, CD, A, B, C and D. This then provides a very simple method for subdomain matching, i.e., a molecule might have EGF's very similar to A, B and C but no fourth domain, or might have a different fourth domain from D and yet still be rapidly returned as a potential match.

The relationship between organizing molecular structural information by the field metric and by EGF's is synergistic. For example, rather than start with random positions for the EGF's, the algorithm will run much faster if one starts near the final solution. If one can use the overlap metric to pull up a similarly shaped molecule that has already been EGF-processed, it is very likely that the EGF composition of this molecule will form a good starting point. Similarly, if one needs shape space coordinates of a molecule relative to a set for which shape space has been characterized, then it is better to start by calculating distances to molecules that are close in shape. The EGF breakdown of the new molecule, when compared to that of those within the database, provides an "initial" embedding, i.e., by finding its rough position within the shape space.

In addition to representing shapes of molecules one can also use the EGF's to compare properties of the underlying atoms, i.e., to solve the "assignment problem", i.e., which atoms correspond to each other between two molecules. This is because when one compares two EGF's there are no ambiguities in their relative overlay (save for a four-fold degeneracy from rotations about the major and minor axes, i.e., there are just four ways to overlay two EGF's). As such one can either directly compare atoms belonging to each EGF (e.g., find distances from similar types of atoms to each other), or one can project such properties onto the pseudosurface of each ellipsoid. I define a pseudo surface of an EGF as the surface of an ellipsoid that has axes in the same direction as the EGF and with the same relative axis (i.e., a/b/c) as the EGF, and which has the same volume as the EGF. (The volume of an EGF, or any field function, is the integral of that function over all space). This also then defines an object that can be graphically displayed as representing the EGF, and this is included in the body of my software. Properties associated with the surface of the EGF could be the electrostatic potential at each point, the distance from the nearest hydrogen bond acceptor etc. The difference between the properties "painted" on the surfaces of two EGF's is a measure of the similarity of these two EGF's with respect to these properties and also forms a metric. As such, an alternate method of storing molecular information is on the basis of this metric, such that one can perform sublinear searches to find similarly "painted" EGF's.

Advantageously, the fields, metrics and ellipsoids I have been discussing can be used in drug design. If the structure of the "active site" of a target protein is known, this can be used to guide the design of the drug molecule. This is because drugs tend to "fit" into the active site, i.e., there is a "lock and key" or "hand in glove" relationship between the shape of the drug and the shape of the active site, which is often a cleft or groove-like. In addition to representing the field of a molecule, one can also use EGF's to represent the "absence" of a molecular field. A long-standing theoretical challenge has been how to represent the space in these binding pockets, since a representation of such can then be used as a template to fit possible tight binding drug molecules. Such an approach, using spheres of varying size, has been used for over a decade in the program by Kuntz known as DOCK, (the procedure of estimating the binding arrangements of a small molecule in a protein pocket is known as "docking").

Instead of using spheres to represent the vacant space in active site protein pockets I use EGF's. The functional form that I use to adjust the centers, axes, and axis magnitudes of the EGF is such that for a spherical EGF the correct distance of approach to an atom of similar radius is reproduced. Such a function has already been devised for this purpose, although other functions may perform better.

Given a representation of the protein pocket in terms of EGF's, which may well be painted with the properties of the protein atoms in proximity to each EGF, the process of finding a match in a database of structures which have been decomposed into EGF's becomes a matter of matching EGF's, painted or not. This can be done by taking combinations of EGF's from the pocket and treating this as the "target". Since the number of EGF's for any pocket is expected to be small, and because my proposed search strategies are "sublinear", I anticipate that this will be practical for libraries of compounds in excess of one billion structures. This will dramatically simplify the process of finding both potential tight-binders and also initial starting points for docking algorithms for predicting binding orientations. It will also help design libraries of compounds biased towards fitting a particular protein pocket by selecting those compounds likely to have similar EGF's to those filling the active site.

IMPLEMENTATION AND EXAMPLES

Specific implementations and examples of the foregoing include the following:
1: Finding the Maximal Overlap (Minimal Field Difference) Between Two Fields A and B
2: Defining the Search Position Via Numerical or Analytical Derivatives
3: Determining the Shape Space of a Set of Molecules
4: Calculating the Position of a New Structure in a Preconstructed Shape Space
5: Extending the Shape Space
6: Calculating the Maximal Overlap Between a New Structure and a Large, Previously Shape-Space Decomposed Set of Molecules
7: Using the Shape Space Description to Correlate with Known Biological Activity
8: Examples of Using the Minimum Field Difference Metric to organize a Database of Molecules
9: Examples of Using the Shape Space Positions to organize a Database of Molecules
10: Local Domain Decomposition
11: Constructing An Ellipsoidal Gaussian Representation (EGR).
12: Construction of Multiple EGR's Containing the Same Number of EGF's.
13: Constructing Molecular Fragments From An EGR.
14: Evaluating An EGR Fit: the Fragment Adjusted EFF.
15: Construction of Multiple EGR's with Different Numbers of EGF's
16: Storage in a Database
17: Comparing Single EGR's to Solve the Atom Assignment Problem
18: EGF Pseudo-Surfaces and Painted EGF's
19: Using a Database of EGR's For (Molecular/Molecular Fragment) Similarity Evaluation
20: Using EGF's in Similarity Searches
21: Using EGR's to Find a Place in Shape Space; Using Shape Space to Find EGR's
22: Defining An EGR For a Negative Space 1: Finding the Maximal Overlap (Minimal Field Difference) Between Two Fields A and B
a) Exhaustive Search The optimal overlay of two molecules depends upon six variables, i.e., three translational degrees of freedom and three rotational degrees of freedom. Since the time taken for any search technique rises as the power of the dimensionality, the problem of optimal overlay is computationally expensive. However, the metric property of the field difference allows for certain improvements in performance because of the triangle inequality. Thus suppose I am trying to overlay molecule B on molecule A and I already have one relatively "good" overlay, with a field difference value of d. Suppose I have just calculated the field difference value for a particular orientation and central position of B with respect to A, d', which is greater than d. I am now in a position to determine which orientations and central positionings relative to this orientation and positioning might have a field difference of less than d. To see this note that the triangle equality lower bound on metric properties states that:

$$|d(AB) - d(BC)| \leq d(AC)$$

where d(AB) is the field difference between molecule A and molecule B at a given orientation and translation relative to each other, and similarly for d(BC) and d(AC), and the |...| symbol of the left hand side indicates the positive value is taken for the difference.

Now I am free to decide that molecule C is actually molecule B, but at a different orientation and separation, call it B'. The inequality then reads:

$$|d(AB)-d(BB')| \leq d(AB')$$

i.e., I have a limit on how much better the overlap of B' can be with A than that of B with A, given that I know the overlap of B with itself, but at a different orientation and separation. But this quantity, d(BB') is independent of A, i.e., depends only upon B. Hence it could have been calculated before the overlap with A was considered, and indeed can be reused in finding the best overlap with molecules other than A. The use of d(BB') is that if the left hand side of the preceding equation is still greater than the best (lowest) value of the field difference so far, then there is no need to calculate the overlap quantity of A with B'.

Figure 5:
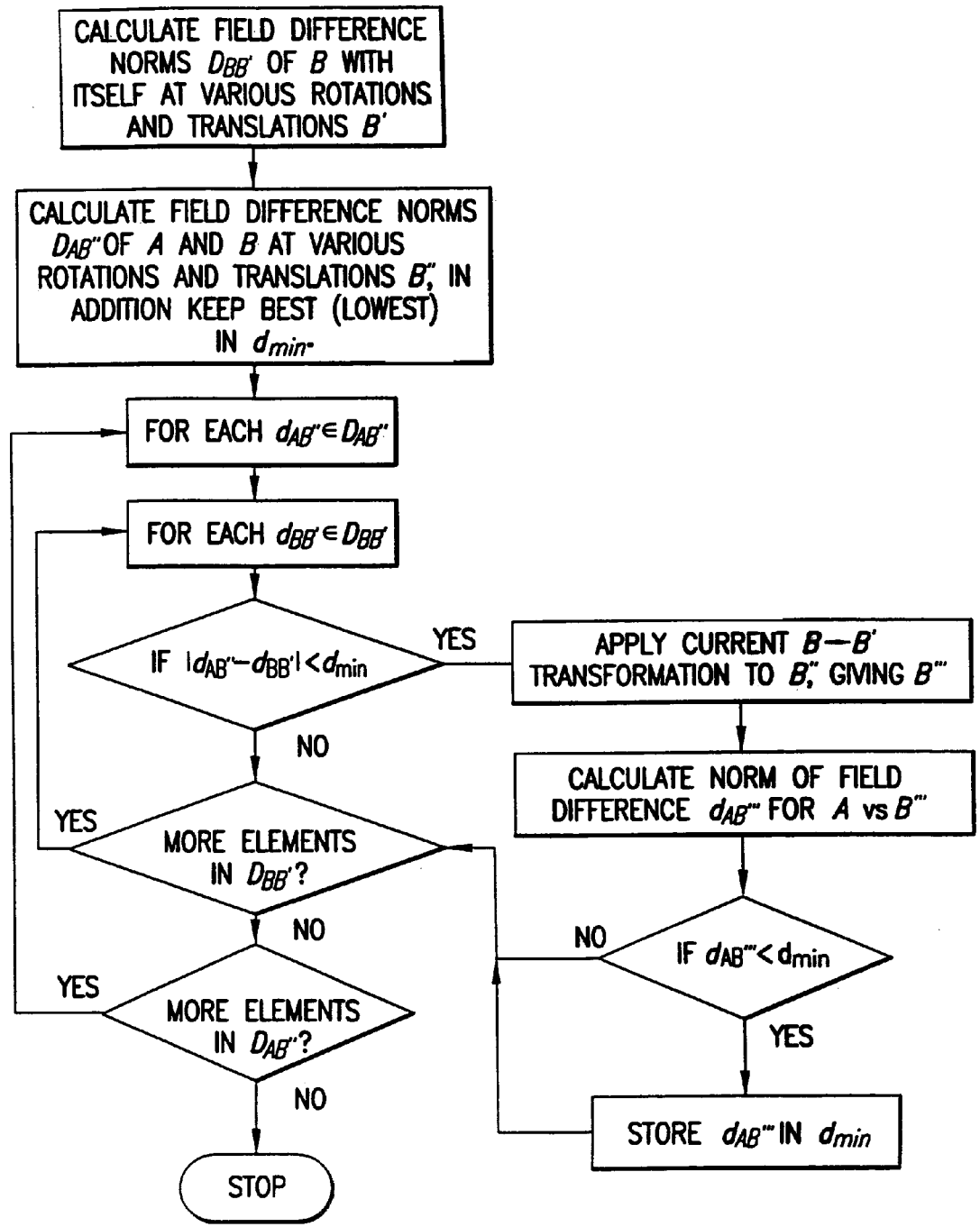
FIG. 5 is a flow chart illustrating one aspect of the invention.

As illustrated in the flow chart of FIG. 5, an example of a procedure to use the metric property of the field overlap is then as follows:
  (i) Calculate the field difference norms of B with itself at a series of orientations and separations, B'. Each new orientation and separation is described by a rotation and translation matrix, respectively. Store the field difference norm along with the rotation and translation matrices, and along with any other information on molecule B. Note that in practice this set of orientations and separations will range over all such that give an overlap greater than some critical value close to zero.
  (ii) Find what might be a good overlay between A and B so as to establish a reasonable value of d. One does this by trying a set of translations and orientations, B", to coarsely sample all reasonable overlays (as in (i), this means that the overlap is greater than some small threshold value), and setting $d_{min}$ equal to the best such value obtained.
  (iii) Sample around each such overlay tried in (ii) using translations and rotations B''' of B" from these positions as precalculated in (i), such that the triangle lower bound can be used to prevent needless calculation of possible overlays.
  (iv) Accept the best overlay from (iii) as the best possible overlay, or select the best N such as candidates for further refinement, e.g., via numerical optimization as described below.
b) Selective Search Align the two fields based upon aspects of the structures or fields that suggest this alignment might be good. For instance, if the two molecules are long and thin then it makes sense to align them such that these axes are in the same direction. Other examples might be to align similar chemical fragments. In my approach I calculate quantities such as the center of mass and the moment of inertia and use these to align the molecules.
  (i) Calculate properties, e.g., center of mass and moment of inertia for A and B.
  (ii) Translate and rotate B to match its properties to those of A, i.e., superimpose the centers of mass, and align the moments of inertia. Techniques for this are known in the art.
2: Refining the Search Position via Numerical or Analytical Derivatives Since a field overlap is defined for all relative orientations and separations, one can calculate derivatives of this function with respect to such variables. These are then used to adjust the relative orientations and separations such as to minimize the field difference (maximize the overlap) by any number of standard numerical techniques, e.g., steepest descent, conjugate gradient, Newton-Raphson etc. If the field is explicitly defined (i.e., as values on a grid) the gradient quantities are calculated numerically by standard techniques. If the field is defined functionally, derivatives may be obtained either analytically or via numerical approximation.

3: Determining the Shape Space of a Set of Molecules

Figure 6:
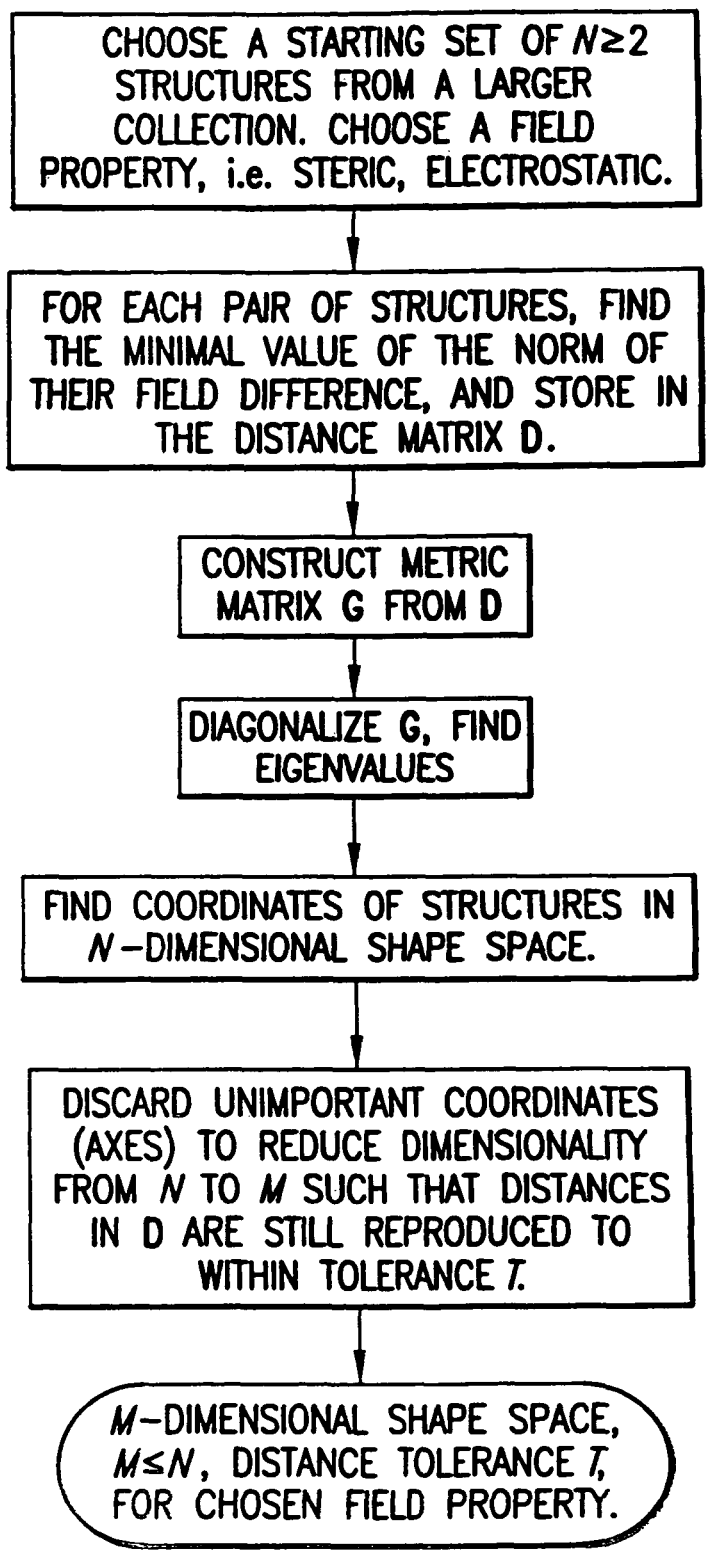
FIG. 6 is a flow chart illustrating a second aspect of the invention.

As illustrated in the flow chart of FIG. 6, the shape space of a set of molecules is determined by the following steps:
  (a) Calculate the maximal overlap (minimal field difference) of all pairs of N structures that constitute my initial set. Note than N will not be the total set of molecules and may be as small as two.
  (b) Given that the norm of the minimal field difference between any two molecules is a metric distance, construct the distance matrix D, where the element ij of D is the minimal field difference between molecule i and molecule j.
  (c) Construct what is known as the metric matrix G from D, as described in any description of distance geometry, e.g., Blaney and Dixon, "Distance Geometry in Molecular Modeling", *Reviews in Computational Chemistry*, Volume V, VCH publishers, 1994, incorporated herein by reference.
  (d) Diagonalize G using any standard technique to find the eigenvalues of a matrix.
  (e) From this diagonalization procedure find a set of positions in N−1 dimensional space that reproduce the distances in the matrix D (see the Blaney/Dixon reference for details)
  (f) Determine which coordinates can be set to zero for each and every molecule and still enable the distance matrix to be reproduced to within a given tolerance T. (This is equivalent to setting all eigenvalues of absolute magnitude less than some cut-off value to zero). The procedure for this is to a) set all the coordinates I want to keep to zero, b) find the geometric center (average coordinates) of the remaining coordinates (the ones I might be able to discard), c) find the largest distance from this center to any one point. d) ascertain if this distance is less than 0.5*T, if so I conclude I can discard these coordinates. (Alternatively, I find the two most widely separated points in the set and determine if the distance between them is less than T. However, this is a more time intensive procedure).

In doing so I determine the M dimensional subspace that the N molecules occupy, subject to tolerance T, where M≦N−1. This is the shape space for the field property used to derive the minimal field differences.

A shape space, once determined, allows for various geometric characterizations of that space and the molecules whose positions have been determined within that space, a characterization that would not have been possible otherwise. These typically involve the degree of uniformity in the coverage of the shape space so defined, which is a useful concept since it relates to the extent this set of molecules represents all possible shapes defined by this shape space. Examples of such characterizations include:
  (i) The volume each molecule occupies within the shape space that is closer to it than to any other molecule in the set, i.e., the Voronoi volume. This can then be used to "cull" those molecules with very small neighborhoods, i.e., which are most redundant within that shape space.

The distribution of the Voronoi volumes also gives a measure of the uniformity of coverage of the shape space.

(ii) The largest void within the space, i.e., the largest hypersphere of the same dimensionality as the shape space that can fit between molecules. This can be used to ascertain which molecules from another set would best fill that gap and hence make the coverage of shape space more uniform.

(iii) The volume of the space occupied by the complete set of molecules (i.e., the volume of what is known geometrically as the "convex hull" defined by those points in the shape space). This quantity is useful in the context of deciding what fraction of the shape space a subset of molecules covers compared to the complete set.

(iv) The smallest subset of molecules which reproduces (iii), i.e., molecules whose shape space positions lie on the convex hull of that set of molecules. These molecules define the boundaries of shape space and hence are useful as the smallest subset of molecules which has the same shape space volume as the total collection.

(v) The local dimensionality around a particular molecule. Given a distance cut-off and a particular molecule, I can calculate the dimensionality of the local shape space of the set of molecules consisting of this molecule and all those closer than the cut-off. The use of this is that certain subsets of molecules may embed within the global shape space in a space of much lower dimensionality (imagine a set of points lying on a curved surface in 3 dimensional space; the global dimension is 3 but the local dimension is 2). This has import for the efficient storage of the shape information of molecules.

4: Calculating the Position of a New Structure in a Preconstructed Shape Space

Once I have a shape space for N molecules, of dimension M, the next step is to calculate the position within this shape space for a molecule not used in the construction of that shape space. This position is found by analogy with triangulation in three dimensions, i.e., if one has a set of distances from an object to four reference objects the exact position can be ascertained. In two dimensions one needs three distances. In M dimensional shape space one needs M+1 distances. (In each of these cases, the M+1 distances must be from points which cannot as a set be described at a dimensionality less than M, e.g., for the case of three dimensions, the four reference points cannot all lie in a 2 dimensional plane). The actual procedure for going from distances to a position is simply that a linear equation for the coordinates can be generated from each distance, such that the solution of the set of such produces the position. This set of linear equations can be solved by any standard method, for instance, Gauss-Jordan elimination (see, for example Stoer and Bulirsch, "Introduction to Numerical Analysis", 2nd Ed., Springer-Verlag, chapter 4). An important note here is that this procedure can fail, i.e., it will produce a position which will underestimate the M+1 distances by a constant amount. This is an indication that the structure under study actually lies in a higher dimensional space than the shape space previously constructed. As such, that shape space needs to be extended.

5: Extending the Shape Space

If the position determining procedure fails, then it is necessary to increase the dimensionality of the shape space description. This is straightforward to accomplish in that I merely need to add an additional variable to all the previous positions, set the additional variable to zero for these structures, and to then find what the new M+1 coordinate for the new molecule needs to be such that the new coordinates now reproduce the distances correctly. But this is simple to calculate from the shortfall in distances calculated by the previous method, since there is only the need to add one more coordinate.

6: Calculating the Maximal Overlap Between a New Structure and a Large, Previously Shape-Space Decomposed Set of Molecules Suppose I have a set of N structures for which a shape space decomposition of dimension M is known. If I have a new structure and wish to find the closest such structure within this set I could use the minimal field distance method between this one molecule and all molecules within the set. Many of the ideas within this document concern how to avoid doing this since N may be very large. An additional component is avoiding the performance of more applications of the minimal field distance method than are necessary.

(i) Determine the shape space position of the new structure as previously described.

(ii) Once the position in shape space is calculated then the procedure to calculate the minimal field difference to any other molecules from within the set (i.e., other than the M+1 used to find its shape space position) is much simpler, i.e., it is just a matter of calculating the distance from the position assigned this new molecule and those positions already calculated for any of the N molecules in the set.

(iii) Since this is simply the square root of the sum of the differences squared for each coordinate, it only involves on the order of 2*M arithmetic operations, i.e., is likely to be several orders of magnitude faster than the minimal field distance method.

7: Using the Shape Space Description to Correlate with Known Biological Activity Partial Least Squares (PLS) analysis is a method of calculating the importance of a set of quantities in determining some "resultant" property. For instance, one might have a set of measurements of physical properties for each member of a set of compounds and wish to know the correlation of each property with the biological activity in some assay. PLS returns a set of weights for each input property such that the activity results can be reproduced from the input values. These then quantify the correlation of the input quantities with the activity and can be used to predict the activity of molecules for which the input quantities are known, but not the biological activity. The use with the shape space decomposition is as follows:

(i) Calculate the shape vector for each molecule for which a biological activity value is known. Note here that the shape vector can be relative to a shape space defined by a completely separate set of compounds, or to the space calculated from that very set of compounds.

(ii) Use the numbers that make up this vector as input to a PLS procedure, with or without other quantities known for each molecule under consideration.

(iii) Use the resultant "weights" to predict the activity of other molecules not in the original set, i.e., by calculating their shape space vector.

Note that more than one shape field can be used as input to a PLS calculation, i.e., the shape vector for the electrostatic field as well as that for the steric field.

8: Examples of Using the Minimum Field Difference Metric to Organize a Database of Molecules Required is a set of N molecular structures. (These will belong to L molecules where L can be less than N if there is more than one conformer of a molecule in the set.) These structures may also have unique chemical identifiers (e.g., chemical names, SMILES strings, catalog numbers etc).

Constructing and Using a Distance Tree
   (i) Choose a structure at random from the N possible structures.
   (ii) Find the field distances from this root structure to all N−1 other structures.
   (iii) Calculate the median of the distances found in (ii).
   (iv) Use the median value as a threshold distance T to subdivide the N−1 other structures into two lists, or "branches", based upon this criterion, with the lower branch containing all structures with distances below the threshold, and the upper branch containing all structures with distances greater than the threshold.
   (v) Store the threshold value along with the root structure in the root node data structure.
   (vi) Repeat this process for each list from i) onwards, but with N decremented by one until the repeatedly divided trees are of size one or zero.

Now, faced with a problem of finding the closest structure in the database to a novel example, i.e., one not in the database, I proceed as follows.
   (i) Find the distance to the root structure.
   (ii) If this distance is less than half the threshold distance (T/2) for this node, then I need never check any structure along the upper branch of the tree, which contains structures whose distance from the root is greater than that threshold, since by the lower bound of the triangle inequality none of them could be as close to the test structure as the root structure is.
   (iii) If the distance to the root structure is more than T/2, I must check the structures on both branches.
   (iv) For each branch selected in (ii) and (iii), the structure in the next node is made a new root structure, and the process repeats starting at step (i), continuing until all relevant branches have been checked.

Typical searches based upon this procedure reduce the number of structures to be actually checked, ideally around the logarithm of N multiplied by some constant factor.

Ordered Lists
   A. Creating the lists.
   (i) (Optional) Determine the shape space of a set of N structures.
   (ii) From the set of N structures, select K key structures that are quite different from each other (i.e., are remote from each other in shape space). For instance, the structures may simply be different from each other in total volume, or be chosen by more computationally intensive methods, e.g., as representatives of clusters of molecular shapes found by standard clustering techniques (e.g., Jarvis-Patrick, etc). These more sophisticated methods may be greatly speeded if the shape space has been determined.
   (iii) For each of the K key structures, find the minimal distance m from it to every other structure in the database. If K is large, this step may also be speeded if the shape space has been determined, allowing simple distance calculations rather than complete overlay calculations for every structure.
   (iv) For each of the K key structures, create a list associated with it, and place into the list, in order of increasing distance, references (name, number etc) to each database structure along with its distance m from the key structure.

B. Using the lists to find the structure closest to a test molecule.

Figures 7A, 7B:
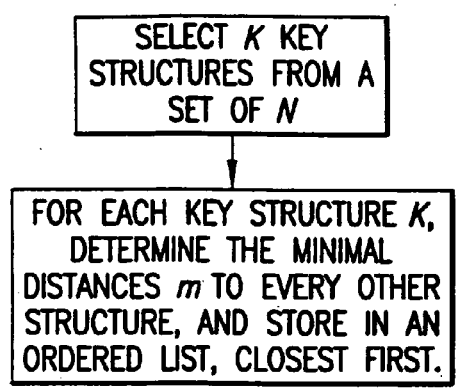
FIGS. 7A and 7B show flow charts illustrating a third aspect of the invention.

As illustrated in the flow chart of FIGS. 7A and 7B, the closest structure is found by the following steps:
   (i) For a test molecule, find its minimal distance x to each of the K key molecules.
   (ii) Choose the list whose key molecule k is closest to the test molecule, where this distance is X. Since the list has molecules close to k first it is likely these are also close to my test molecule.
   (iii) Set as current list position n the top of list k. Set a variable BEST equal to X
   (iv) Otherwise, if the distance m from key k to list structure n is greater than X+BEST, then stop, as by the lower bound of the triangle inequality no structure further down the list can be closer to the test molecule than STRUCT, i.e., if m=X+BEST+a for any positive distance a, then the triangle inequality |m−X|<d can be rewritten as d>BEST+a.
   (v) Find the minimal distance d from the test molecule to the current structure n on the list.
   (vi) If d<BEST, store d in BEST, and n in STRUCT.
   (vii) If more structures, increment the list position n by one and continue at (iv).
   (viii) When the procedure terminates, the index n of the closest structure to the test molecule is found in STRUCT.

Thus I can search the database, by minimum field difference, in a time sublinear with the number of molecules in the database. This is because, by the triangle inequality, I know the cutoff distance for evaluating structures in the list is at most equal to 2× (when BEST=X) and is potentially further refined as I progress down the list and find better (smaller) values for BEST. As noted above, the list creation process can be speeded if the shape space of the structures has already been determined. Whether the time saved will be justified by the time spent constructing the shape space depends on the number of key structures K and the number of structures in the database.

9: Examples of Using the Shape Space Positions to Organize a Database of Molecules Making and Using an M-Dimensional Tree M dimensional data points may be stored in a tree-like data structure such that an efficient search can be made to find all points within a distance d of a new point. These algorithms are standard in art. Although the performance of this tree lookup is not guaranteed efficient, i.e., there are pathological cases where it is no better than testing all points, on the average it allows the number of search steps to be reduced from N (the number of points in the tree) to some multiple of the logarithm of N.

1) Constructing and using an M-dimensional tree.
   (i) Find the shape space positions for a set of N structures.
   (ii) Choose a structure at random from this set and record its name in the zero level node of a tree structure which is such that each "node", or "slot", has two child nodes, called "left" and "right", at what I refer to as a level one greater than this node.
   (iii) Select a second structure at random and store its name in either the left level one node of the tree if its first shape space coordinate is less than that of the first structure, otherwise place it in the right level one node.
   (iv) Chose another structure at random. As before, test its first shape space coordinate. This time, however, if the node it should be placed in is already occupied, place it under that node, i.e., level two, in either the left or right hand node based upon comparison to the second shape space coordinate of the node it now lies under.
v) Continue in this fashion, where the right-left decision is based upon the level of the node it is to lie under. If that level is greater than M, then the test coordinate is equal to the depth of the tree, modulo M, i.e., on the M+1 level the coordinate used to test upon returns to the first coordinate, M+2 to the second etc.

2) Searching an M-dimensional Tree
(i) Find the shape space position of the new structure for which a similarly shaped molecule is required.
(ii) Perform the following test: is the first coordinate of the new structure within distance d of that of the zero level structure? If not, is it (a) greater than or (b) less than that coordinate of the zero level structure?
(iii) In the first instance calculate the distance of the zero level structure to the new structure, adding it to a "hit" list if it is closer than d.
(iv) In the second instance (a) I can now discard all structures lying under and including the left node from consideration
(v) In the third instance (b) I can discard all structures lying under and including the right node from consideration.
(vi) Test the structures assigned to nodes on level one remaining (after the test in ii)
(vii) Perform the same test as in (ii)-(v) on each of these structures, except that the test is now performed using the second coordinate.
(viii) Proceed down the tree, adding the "hit" list where appropriate, culling portions of the tree were possible until all structures have either been tested for addition to the list or culled.

In (1) above, rather than choosing structures at random for insertion into the tree, they could instead be sorted into a list, for example in order of increasing volume, and then taken sequentially from the list for insertion into the tree. This allows additional criteria to be used to terminate a search of the branches of the tree.

10: Local Domain Decomposition

The overlay of molecular fields is a method of finding global similarities between molecules, i.e., whether molecule A has the same distribution of properties as molecule B. While this is extremely useful, it is also the case that local similarities are of interest, i.e., when a part of molecule A is similar to a part or all of molecule B. The methods described below are an approach to solve this problem by defining representations of parts of a molecular field which have an approximately ellipsoidal character. These representations conform to visual and chemical intuition as to possible fragmentations of a molecular structure, and can be compared between molecules either singly or in combination with ease.

11: Constructing An Ellipsoidal Gaussian Representation (EGR)

An Ellipsoidal Gaussian Representation (EGR) of a molecular structure is constructed by fitting one or more Ellipsoidal Gaussian Functions (EGF) to a field function of a molecule, for instance a steric or electrostatic field.

A variety of methods can be used to find the optimal parameters for one or more EGF's so as to minimize the EFF. Two such methods for calculating the EFF for a given set of parameters for each EGF are:

1) Numeric:
(i) Define a grid of regularly spaced points (a lattice) large enough so that it contains all points for which the functional value of the molecular field and/or the EGR field has an absolute value greater than zero by a given amount. For example, choose the extent of such a lattice such that all atom centers and all EGF centers are within the boundaries of the lattice by a given distance.
(ii) Calculate the square of the difference at each grid point and sum over all such points.

2) Analytic:
(i) Define an analytic description of the molecular field. An example would be the steric field generated by representing each atom by a Gaussian function (defined above) and forming the sum or exclusion product field (defined above) from each such Gaussian.
(ii) Given such an analytic description the EFF becomes the sum of a series of integrals since the square of the difference field is now a sum of integrable functions. If the molecular field is defined from Gaussian functions, then the integrals are of a particularly simple form.

Given a procedure to calculate the EFF, the EGF parameters can be optimized to minimize the EFF. Standard methods exist in the literature for such an optimization, whether the EFF is calculated numerically or analytically.

Of significance to the practical implementation of any method are the initial EGF parameters. My work suggests that the initial parameters must be such that there is significant overlap between the each EGF and the molecular field. Thus, my typical starting configuration is a center for each EGF within the molecule (defined as within an atom's radius of at least one atom within the molecule), with axes A, B and C set to the x, y and z Cartesian axes, and widths u, v and w set to 1.0, and prefactor p set to 1.0.

12: Construction of Multiple EGR's Containing the Same Number of EGF's.

Most methods of optimizing EGF parameters, such as minimizing the EFF, suffer from one drawback, namely that they converge to a set of parameters that do not necessarily correspond to the lowest possible EFF value, rather such parameters are "locally stable", i.e., any small change in any one parameter results in an increase in the EFF value. Such "multiple minima" are intrinsic in the nature of the problem. The local minimum with the lowest EFF value is referred to as the "global minimum". I utilize the multiple minima nature of the problem in that I do not necessarily require a single EGF for a particular molecular structure, in fact I welcome multiple representations for uses described later in this document.

Procedure:
(i) Choose how many EGF's I want in the EGR.
(ii) Find the EGR by optimizing the EGF parameters to minimize the EFF.
(iii) Add the characteristics of this EGR (i.e., the EGF parameters) to a list of possible EGR's.
(iv) Find a new EGR by repeating (ii) but with different starting positions (which, as described above, are chosen to have random centers within the molecule).
(v) Compare this EGR's characteristic to all those on the EGR list.
(vi) If these characteristics are "similar" to any on the list discard this EGR, otherwise add it to the list. "Similar" here can be defined as having EGF parameters that differ by no more than a preset amount. If the EGR is discarded I increment a parameter "OLD" by one, otherwise set OLD to zero.
(vii) If OLD is equal to a predetermined number END, I quit the procedure, otherwise I return to (iv), i.e., if I have not generated a new structure in the previous END tries end the procedure, otherwise try again.

13: Constructing Molecular Fragments from an EGR

Given an EGR containing more than one EGF, a procedure of particular utility is to assign each atom in the molecular structure to a particular EGF. This assignment operator can have various forms. The form I have adopted is as follows:
  (i) For each atom calculate the EFF of the functional form representing that atom's contribution to the molecular field with each EGF in turn.
  (ii) Based upon these "atomic-EGF" EFF's, assign each atom to the EGF for which its EFF is lowest.
  (iii) The collection of atoms assigned to a particular EGF forms a set referred to here as a molecular fragment, or subdomain.

14: Evaluating an EGR Fit: the Fragment Adjusted EFF

Given that the number of EGF's I include in an EGR is a variable, there is an infinite number of possible EGR's for a molecule. When comparing two different EGR's with the same number of EGF's I can use the EFF as a guide to which representation is the more appropriate representation, i.e., lower EFF means a better fit. Comparing EGR's with different numbers of EGF's is more problematic because the number of adjustable parameters is proportional to the number of EGF's, hence the more EGF's the lower the EFF tends to be. Yet, more EGF's in an EGR are not necessarily a more useful domain decomposition since this will ultimately tend towards one EGF per atom. Decomposing a molecule into each of its component atoms is a trivial exercise of little utility. A more useful measure of fit can be obtained as follows:
  (i) Calculate the molecular fragments induced by the EGR as described above.
  (ii) Calculate the EFF of the field produced by each molecular fragment with the EGR to which it has been assigned.
  (iii) Sum these domain EFF's together to form a quantity I will refer to as the "sum fragment EFF."
  (iv) Calculate the EFF of the whole molecule's field vs. its EGR. I will term this quantity the "molecular EFF."
  (v) Add together the sum fragment EFF and the molecular EFF to form what I refer to as the "fragment adjusted EFF."

Although the fragment adjusted EFF typically is smaller for two EGF's versus one, I have observed that as the number of EGF's further increases, the fragment-adjusted EFF eventually starts increasing again. The number of EGF's for which the best obtained EGR has the lowest fragment adjusted EFF is defined as that structure's optimal EGF count.

15: Construction of Multiple EGR's with Different Numbers of EGF's

In light of the above, the procedure for generating a set of EGR's that covers possible domain decompositions of a molecular structure is then as follows:
  (i) Set the number of EGF's in the EGR to one.
  (ii) Perform the "multiple EGR" procedure as described above.
  (iii) Store each EGR so generated as a representation of the molecular structure.
  (iv) Find the best fragment adjusted EFF amongst the EGR so generated.
  (v) If the number of EGF's used in (ii) is equal to one set the parameter "BEST" equal to this fragment adjusted EFF.
  (vi) If the number of EGF's used in (ii) is greater than one check to see if this fragment adjusted EFF is greater than BEST. If so then quit the procedure, otherwise increment the number of EGF's to be used in (ii) by one and return to (ii).

16: Storage in a Database

The utility of having various EGR's for a single structure is limited. The true utility comes in using the information contained in the EGR to compare different structures. Typically this will involve finding aspects in common between a single structure and a set of structures, each of which has had an EGR decomposition performed and the parameters that describe each EGR stored in association with a unique identifier for that structure (e.g., the structure's name, number). The way the EGF information is stored and retrieved can determine the efficiency and utility of its use, as is typical of all database applications. Below are described examples of such database applications.

17: Comparing Single EGR's to Solve the Atom Assignment Problem

A recurrent problem in the comparison of molecules or parts of molecules is known as the "assignment" problem. Put simply, it is to associate each atom from one molecule with an atom in a second molecule. Given an alignment between two molecules the assignment problem can be solved via such operators as "closest" or "closest of similar type", where type might be element type or any number of characterizations of an atom. However, choosing the alignment that in some way optimizes some characteristic of the assignment is a hard problem, since there are an infinite number of possible alignments. However, the EGR does provide one solution, as follows:
  (i) Calculate an EGR for molecule X and molecule Y.
  (ii) Each EGF within an EGR has a center (a, b, c) and an orientation defined by axes A, B and C.
  (iii) Orient an EGF from the EGR of molecule Y such that the center and axes of Y coincide with that of X. The alignment of the axes is such that the axis from X with the largest value from its u, v, and w values is aligned with the axis from Y with the largest of its u, v and w values and similarly for the smallest of such coefficients. There are actually four different ways this can be achieved, given the symmetry of an ellipsoidal function.
  (iv) For each of the four alignments, make the atom to atom assignments for the atoms which belong to the pair of EGF's being aligned together based upon "closest" or "closest of similar type".
  (v) Rather than have an infinite number of possible alignments I now have just four to choose from, and given any kind of measure for the assignment (e.g., minimize the sum of the distances of each atom pair) this is straight-forward.

Note that if the number of EGF's for X and Y is one then this provides a match between all atoms of X with all of those of Y. Otherwise, the choice of EGF's from X and Y induce a partial match between X and Y. Given a measure of the quality of this partial assignment, all possible combinations of EGF's between X and Y can be chosen to find the best EGF induced assignment.

18: EGF Pseudo-Surfaces and Painted EGF's

Rather than compare molecular fragments via an atom assignment procedure one can compare the properties in the vicinity of each fragment. To do so I introduce the concept of an EGF pseudo-surface. The concept is simple enough, namely that just as a spherical Gaussian function (i.e., an EGF where the widths u, v and w are all equal) is the field function for a single atom, which is normally thought of as having a surface at that atom's radius, so I can associate an ellipsoidal surface with each EGF. This surface can be thought of as an isovalue contour of the EGF, and as such has the same shape implicit in the EGF representation. I have found that creating this ellipsoidal contour such that it has the same volume as that of the EGF is effective in enclosing the atoms belonging to that EGF. The procedure is as follows:
  (i) Calculate the volume of the EGF (the volume of an EGF is defined as the integral of that function over all space).

(ii) Find the factor R such that an ellipsoid with axes (R/√(u), R/√(v), R/√(w)) would have the same volume as the EGF.

(iii) Define the pseudo-surface of the EGF as the surface of the solid ellipsoid defined in (ii) which has its center coincident with the EGF and its axes aligned along A, B and C of that EGF (the axis of length R/√(u) is aligned with axis A, the axis of length R/√(v) is aligned with axis B, the axis of length R/√(w) is aligned with axis C).

The use of the EGF pseudo-surface lies in the fact that if properties are assigned to each point on this surface, then such properties can be compared with those belonging to a different EGF pseudo-surface. I refer to an EGF with a pseudo-surface that has properties associated with it as a "painted EGF". Properties can "paint" an EGF in a variety of ways, for example:

(i) Be analytically defined on the surface of the ellipsoid from the underlying analytical form of the property.

(ii) Be calculated at a number of "sample" points distributed on the surface of the ellipsoid, either from analytic functional forms of the property, or interpolated from values of the property at nearby points in space (e.g., from a grid of values).

(iii) Be assigned values at sample points based upon proximity to underlying atoms, e.g., the atomic properties are "projected" to this surface.

The information in the pseudo-surface values at a set of points (as in (ii) above) may be stored in several ways. (a) The first is just as a list of values associated with each point. (b) If the values at points are of binary nature (one or zero) then the storage may take the form of a bit-pattern. (c) The pattern of values at points may be transformed into an approximate functional form, typically spherical harmonics, i.e., an analytic form as (i) above. (d) Finally, the patterns may be stored "virtually", i.e., not actually calculated until required but rather "stored" as a method of calculation.

The comparison of the properties "painted" on two such surfaces is as follows:

(i) Align the two EGF's relative to each other in one of the four possible orientations wherein centers and axes are aligned as above.

(ii) Change the shape of each pseudo-ellipsoid to that of a sphere of unit radius via a series of three compressions, one along each axis of the ellipsoid.

(iii) Compare the properties, point by point, of the now identically shaped surfaces and superimposed surfaces.

The comparison step in (iii) can actually be made a metric distance, i.e., if the integral over the difference in properties at the surface of the unit spheres is found, then the square root of this quantity is a metric distance for exactly the same reason the similar quantity is such for three dimensional fields. Technically speaking the field described by a property on the surface of a unit sphere has the mathematical designation $S^2$, as opposed to $R^3$ for a molecular field, but is still a field. However, the problem of finding the minimal distance between two such spherical fields is much simpler in my case than for general $S^2$ fields because the overlay of the ellipsoids only allows for four possible orientations, rather than an infinite number (mine is actually an oriented $S^2$ field).

Given that the properties on the surface of two pseudo-surfaces can be compared via a metric distance, I can apply all of the techniques discussed previously on using metrics to organize such information, now using them for fast similarity searches on pseudo-surface property patterns. I can also form an M dimensional representation of the minimal difference between all pairs of a set of painted EGF's. Note that this is not as useful as in the case where the alignment problem is paramount, since the ellipsoid's alignment only allows for four possible such cases.

19: Using a Database of EGR's for (Molecular/Molecular Fragment) Similarity Evaluation A typical use of an EGR database is to extend the concept of global similarity matches to parts of a molecule, i.e., the local domain match problem. A typical procedure for this is:

(i) Construct a database of EGR's for a set of molecular structures.

(ii) Each EGF in each EGR so generated defines a set of atoms which "belong" to it, hence each EGR defines various molecular fragments. For instance, if EGR 1 contains EGF's A, B and C then there are seven molecular fragments defined, namely those from A, B, C, AB, BC, AC, ABC. Note that the last such is simply the whole molecule.

(iii) Store details of each molecular fragment. Note that such details might include the shape vector of this fragment from a predefined shape space, the nature of the EGF's which "enclose" these fragments, as well as other physical properties.

(iv) For a new structure not represented in this database of molecular structures, generate a set of EGR's and a corresponding set of molecular fragments for each.

(v) For each such fragment search the database generated in (iii) for similar fragments, where "similar" may mean similar in steric shape or any of a variety of other measures, e.g., electrostatic field, hydrogen bond positioning etc. These fragment searches may or may not use metric quantities.

(vi) If such a search generates similarities above a certain, specified level then report these matches either graphically or via a listing to file or screen.

20: Using EGF's in Similarity Searches

In addition to using the fragmentation properties of the EGF's within an EGR, EGF's can also be used to directly aid a similarity search. The following describes a linear search:

(i) Construct a database of EGR's for a set of molecular structures.

(ii) Find the optimal number, M, of EGF's needed in an EGR for the new structure I wish to compare to the structures in this database.

(iv) Construct a set of M EGR's for the new structure, one of each containing 1 up to MEGF's (i.e., if M=3 construct EGR's with one, two and three EGF's).

(v) Find the metric field difference value of the new structure with the first molecule in the database, store this value in the parameter BEST, and store the value one in the parameter BESTSTRUCTURE.

(vi) Retrieve the best EGR description containing M EGF's of the next structure in the database, or if this structure has at most L EGF's in any of its EGR's, the best EGR with L EGF's.

(vii) Compare this retrieved EGR with the EGR with the same number of EGF's from the new structure as follows: Pair the EGF's between the two EGR's by ranking each set by volume, i.e., the "biggest" EGF in the test molecule with the "biggest" EGF in the database structure. Calculate the EFF for each such pair assuming the EGF's are superimposed optimally (i.e., the centers and major and minor axes are aligned). This is easy to do since there is an analytic formula for the EFF of two EGF's optimally aligned to each other. This gives a measure of the best possible EFF that could be expected between the new structure and the current structure from the database.

(viii) If this estimate of the best EFF between the new structure and the current database structure is greater than the BEST parameter go to (v).

(ix) Otherwise actually find the best metric field difference between the new molecule and the current database structure. If this value is less than BEST, set BEST equal to this value, set the value of BESTSTRUCTURE to indicate this structure. Go to (v) unless this is the last structure in the database.

In the above procedure I am using the EGF's that make up the best EGR of a molecule to save time in actually having to calculate the best orientations between two molecules, which is analogous to the use of the triangle inequality of the metric field difference distance. In fact I am using this metric nature, but in a more convoluted way than before.

Note that I can improve on the above method by organizing the structures based upon the EGF's that make up the best EGR for each structure, i.e., such that instead of starting with the first structure in the database I start with the structure which has the most similar set of EGF's ("most similar" defined here as having the most similar volumes). Starting with a structure that is more likely to have a small resultant BEST parameter means that step (vii) is more likely to reject the next structure, i.e., the time intensive step of finding the best overlay is avoided more often. A simple method of organizing the structures such that those with similar EGF descriptions to a test structure can be rapidly found is via an N-dimensional hash table, but many other methods exist in the literature.

21: Using EGR's to Find a Place in Shape Space; Using Shape Space to Find EGR's

There is a synergistic relationship between the shape space concept and the EGR concept in that having one makes finding the other easier. In the following, I assume that a database has been constructed which holds both the shape-space description and the EGR description of each structure.

Given an EGR for a new structure, and requiring a shape space description:
  (i) Use the EGR description to find the structure of most similar shape in the database of structures.
  (ii) Find the minimal metric field difference between this structure and the new structure.
  (iii) Find the next most similarly shaped structure in the database.
  (iv) Find the minimal metric field difference between this structure and the new structure.
  (v) Find the position in shape space assuming that the structures retrieved so far from the database define the whole of the shape space. If the distances between the new molecule and those structures are correctly reproduced then finish the procedure, otherwise go to (iii).

The rationale behind this procedure is that although the shape space dimensionality of the database of structures may be M, the local dimensionality of molecules like the new molecule may be much less than M. As an example, if in three dimensions points lie on a line which is curving through space, and if my test point lies on this line, close to two other points, then the distances to just these two points can define quite accurately the position on this line, not the normal four such points that would be required if the points were randomly distributed in all three dimensions. Hence, given similar structures I find the position in shape space with fewer than M+1 comparisons, if the local distribution of such structures is not smooth in all M directions.

Given a shape space vector of a new molecule but not an EGR
  (i) Find the most similar structure, or set of structures from within a database of such.
  (ii) Use the EGF positions of each of the EGR's associated with each such structure as a starting point for an EFF minimization for the new molecule.
  (iii) Then perform a "normal" EFF minimization but with random starting positions.

The rationale here is that since the structures found in the database are similar then the EGR's will also be similar. If so, much time will be saved in step (iii) because many of the potential EGR's will have already been found.

22: Defining an EGR for a Negative Space

Of particular interest in the use of EGR descriptions is finding molecules that might fit in the active site of a protein, as this is the mode of action of most pharmaceutical compounds. The procedure is as follows:

Finding Active Site EGF's:
  (i) Define a fitting function f between any two EGF's such that if both were spherical this function would be a minimum when the inter-EGF distance is the same as the sum of the radii of each EGF (defining the radii of the EGF as that of a sphere of equivalent volume). Such a function for two EGF's, EGF1 and EGF2, is:

$f = a*V - b*(Q(EGF1, V) - Q(EGF2, V))$ where V=Q(EGF1, EGF2) where Q is defined in equation (6) above.

(ii) Define a molecular field function from either a sum or exclusion product of a set of N atomically centered spherical EGF's, where each such EGF has the same volume as the atom upon which it is placed, and where the N atom centers belong to all of the atoms in the protein within a specified distance of the active site (the active site may be defined in various ways, for instance as consisting of all atoms known to be involved in the function of the active site). It should be noted that the molecular field function generated by the exclusion product method is itself a sum of EGF's, as EGF's multiplied together result in another EGF.

(iii) Minimize a function F which is the sum of functions f defined in (i) over the individual EGF components of the molecular field defined in (ii) each overlapped with a test EGF, where this test EGF is placed at a random starting point in the active site and is initially spherical with a volume set to that of a single carbon atom and where all parameters that define this test EGF are allowed to vary.

$F = \Sigma(f(MolecFieldEGF_n, TestEGF))$ for n from 1 to the number of individual EGF's making up the molecular field.

(iv) Repeat step (iii) with different random starting points until no significantly new final EGF's are generated (criteria for "new" being those used in the generation of a standard EGR).

This procedure produces a series of single EGF descriptions of the active site. These EGF's may be painted, based upon properties of the nearest protein atoms, or of any field quantity generated by such atoms, e.g., electrostatic potential.

Searching an EGR Database for a Fit to the Active Site:
  (i) Form an EGR from the single EGF descriptions generated by the above procedure by combining two or more such EGF's.
  (ii) Treat these EGF combinations exactly as one would those from any molecular EGR in searching for similar molecules, with the one exception that one may want to change the sign of some EGF pseudo-surface properties, e.g., electrostatics so that one finds electrostatically complementary molecules to the active site.

(iii) Use the alignments with any molecular structures found to be similar to this combination of active site EGF's as starting points to procedures to optimize any fitness function of the molecule with the active site (e.g., an energy function, or docking function).

What is claimed is:

1. A method of organizing a database of N objects, wherein the database is stored on a computer, for facilitating searching the database with a query object, the method comprising:

selecting K key objects from the database that differ from one another in their respective values of some property field and wherein K is less than N;

calculating a minimal metric distance between the field associated with each of said K key objects and the respective field associated with every other object in said database; and storing in said database, for each of said K key objects, an ordered list of each database object and its minimal metric distance from said key object, wherein each of said objects is a molecule, wherein each of said fields is fitted by an ellipsoidal Gaussian representation, and wherein at least the calculating is carried out on the computer.

2. The method of claim 1 wherein at least one of said minimal metric distances is obtained by calculating a maximal overlap between one field and another field.

3. The method of claim 1 wherein each of said fields is selected from the group consisting of: a steric field of a molecule and an electrostatic potential around a molecule.

4. The method of claim 1 wherein each of said ellipsoidal Gaussian representations is constructed by:

choosing a number of ellipsoidal Gaussian functions to represent said field, wherein each ellipsoidal Gaussian function comprises a prefactor, three width factors, coordinates of its center, and three mutually orthogonal unit vectors that define the directions of its principal axes;

centering each ellipsoidal Gaussian function at a randomly chosen position within said field;

forcing each ellipsoidal Gaussian function to initially adopt a spherical shape; and maximizing the overlap between said field and the ellipsoidal Gaussian functions by adjusting the coordinates of the center, the orientations of the principal axes and the magnitudes of the width factors and the size of the prefactor, wherein at least the maximizing is carried out on the computer.

5. The method of claim 1 additionally comprising, before said selecting, calculating a shape space of the database of N objects, and wherein said selecting includes selecting key objects that are remote from each other in shape space.

6. The method of claim 1 additionally comprising, before said selecting, applying a clustering technique to the database to obtain one or more clusters of molecules, wherein said selecting includes selecting key structures that are representatives of the one or more clusters.

7. The method of claim 4 wherein said maximizing is calculated by minimizing a value of an ellipsoidal Gaussian representation fitness function.

8. The method of claim 2, wherein at least one of said minimal metric distances is obtained by calculating a maximal overlap between a field on one molecule and a field on another molecule, starting from an orientation of the two fields that is obtained by:

calculating a center of mass and inertia tensor for each molecule; and translating and rotating one molecule so that its center of mass and at least one inertial axis superimpose respectively with the center of mass and at least one inertial axis of the other molecule.

9. The method of claim 2 wherein at least one of said minimal metric distances is obtained by repeated searches from different starting orientations of said first field.

10. The method of claim 9 wherein each of said repeated searches utilizes a numerical technique selected from the group consisting of: steepest descent, conjugate gradient and Newton-Raphson.

11. A computer, configured to organize a database of N objects for facilitating searching the database with a query object, the computer comprising a memory encoded with instructions that, when executed by the computer:

select K key objects from the database that differ from one another in their respective values of some property field and wherein K is less than N;

calculate a minimal distance between the field associated with each of said K key objects and the respective field associated with every other object in said database; and store in the database, for each of said K key objects, an ordered list of each database object and its distance from said key object, wherein each of said objects is a molecule, wherein each of said fields is fitted by an ellipsoidal Gaussian representation, and wherein the database is stored on the computer.

12. A non-transitory computer program product comprising a medium encoded with instructions that, when executed by a computer, cause the computer to organize a database of N objects for facilitating searching the database with a query object, the instructions comprising instructions for:

selecting K key objects from the database that differ from one another in their respective values of some property field and wherein K is less than N;

calculating a minimal distance between the field associated with each of said K key objects and the respective field associated with every other object in said database; and storing in said database, for each of said K key objects, an ordered list of each database object and its distance from said key object, wherein each of said objects is a molecule, wherein each of said fields is fitted by an ellipsoidal Gaussian representation, and wherein the database is stored on the computer.

13. A method of searching a database with a query object, the method comprising:

organizing the database according to the method of claim 1;

identifying the ordered list of objects associated with the key object calculated to be closest to the query object; and calculating distances between the query object and those objects in the ordered list associated with the key object calculated to be closest to the query object.

14. A computer configured to search a database with a query object, the computer comprising a memory encoded with instructions that, when executed by the computer:

organize the database according to the method of claim 1;

identify the ordered list of objects associated with the key object calculated to be closest to the query object; and calculate distances between the query object and those objects in the ordered list associated with the key object calculated to be closest to the query object.

15. A non-transitory computer program product comprising a medium encoded with instructions that, when executed by a computer, cause the computer to search a database with a query object, the instructions comprising instructions for:
organizing the database according to the method of claim 1;
identifying the ordered list of objects associated with the key object calculated to be closest to the query object; and
calculating distances between the query object and those objects in the ordered list associated with the key object calculated to be closest to the query object.

16. The computer of claim 11 wherein the memory is further encoded with instructions for obtaining at least one of said minimal metric distances by calculating a maximal overlap between one field and another field.

17. The computer of claim 11 wherein each of said fields is selected from the group consisting of: a steric field of a molecule and an electrostatic potential around a molecule.

18. The computer of claim 11 wherein the memory is additionally encoded with instructions for, before said selecting, applying a clustering technique to the database to obtain one or more clusters of molecules, and wherein said selecting includes instructions for selecting key structures that are representatives of the one or more clusters.

19. The computer of claim 11, wherein the memory is further encoded with instructions for constructing each of said ellipsoidal Gaussian representations by:
choosing a number of ellipsoidal Gaussian functions to represent said field, wherein each ellipsoidal Gaussian function comprises a prefactor, three width factors, coordinates of its center, and three mutually orthogonal unit vectors that define the directions of its principal axes;
centering each ellipsoidal Gaussian function at a randomly chosen position within said field;
forcing each ellipsoidal Gaussian function to initially adopt a spherical shape; and
maximizing the overlap between said field and the ellipsoidal Gaussian functions by adjusting the coordinates of the center, the orientations of the principal axes and the magnitudes of the width factors and the size of the prefactor,
wherein at least the maximizing is carried out on the computer.

20. The computer of claim 19 wherein the instructions for maximizing comprise instructions for minimizing a value of an ellipsoidal Gaussian representation fitness function.

21. The computer program product of claim 12 further comprising instructions for obtaining at least one of said minimal metric distances by calculating a maximal overlap between one field and another field.

22. The computer program product of claim 12 wherein each of said fields is selected from the group consisting of: a steric field of a molecule and an electrostatic potential around a molecule.

23. The computer program product of claim 12 additionally comprising instructions for, before said selecting, applying a clustering technique to the database to obtain one or more clusters, and wherein said selecting includes selecting key structures that are representatives of the one or more clusters.

24. The computer program product of claim 12, additionally comprising instructions for constructing each of said ellipsoidal Gaussian representations by:
choosing a number of ellipsoidal Gaussian functions to represent said field, wherein each ellipsoidal Gaussian function comprises a prefactor, three width factors, coordinates of its center, and three mutually orthogonal unit vectors that define the directions of its principal axes;
centering each ellipsoidal Gaussian function at a randomly chosen position within said field;
forcing each ellipsoidal Gaussian function to initially adopt a spherical shape; and
maximizing the overlap between said field and the ellipsoidal Gaussian functions by adjusting the coordinates of the center, the orientations of the principal axes and the magnitudes of the width factors and the size of the prefactor,
wherein at least the maximizing is carried out on the computer.

25. The computer program product of claim 24 wherein the instructions for maximizing comprise instructions for minimizing a value of an ellipsoidal Gaussian representation fitness function.

26. A method of organizing a database of N objects, for facilitating searching the database with a query object, wherein the database is stored on a computer, the method comprising:
calculating a shape space of the database of N objects by:
choosing an initial set of N objects;
calculating a distance matrix D wherein each element $D_{ij}$ is a minimal metric distance between object i and object j and wherein said object i and said object j are in said initial set of objects;
constructing a metric matrix G from D according to a distance geometry technique;
diagonalizing G, thereby obtaining eigenvalues of G, and obtaining a set of positions in N–1-dimensional space that reproduce the distances in said matrix D to within a tolerance T, wherein each position of said set of positions has N–1 coordinates associated with it;
removing each of the N–1 coordinates that can be set to zero for every object in said set of objects such that a remaining number, M, of the N–1 coordinates still enables said distance matrix to be reproduced to within said tolerance, T; and
defining the shape space to be an M dimensional subspace occupied by the N objects;
selecting K key objects from the database that are remote from each other in shape space, and that differ from one another in their respective values of some property field, wherein K is less than N;
calculating a minimal metric distance between the field associated with each of said K key objects and the respective field associated with every other object in said database; and
storing in said database, for each of said K key objects, an ordered list of each database object and its minimal metric distance from said key object,
wherein at least the calculating the shape space is carried out on the computer.

27. A computer, configured to organize a database of N objects, for facilitating searching the database with a query object, the computer comprising a memory encoded with instructions that, when executed by the computer:
calculate a shape space of the database of N objects by:
choosing an initial set of N objects;

calculating a distance matrix D wherein each element $D_{ij}$ is a minimal metric distance between object i and object j and wherein said object i and said object j are in said initial set of objects;

constructing a metric matrix G from D according to a distance geometry technique;

diagonalizing G, thereby obtaining eigenvalues of G, and obtaining a set of positions in N−1-dimensional space that reproduce the distances in said matrix D to within a tolerance T, wherein each position of said set of positions has N−1 coordinates associated with it;

removing each of the N−1 coordinates that can be set to zero for every object in said set of objects such that a remaining number, M, of the N−1 coordinates still enables said distance matrix to be reproduced to within said tolerance, T; and defining the shape space to be an M dimensional subspace occupied by the N objects;

select K key objects from the database that are remote from each other in shape space, and that differ from one another in their respective values of some property field, wherein K is less than N;

calculate a minimal distance between the field associated with each of said K key objects and the respective field associated with every other object in said database; and store in the database, for each of said K key objects, an ordered list of each database object and its distance from said key object, wherein at least the calculating is carried out on the computer.

28. A non-transitory computer program product comprising a medium encoded with instructions that, when executed by a computer, cause the computer to organize a database of N objects for facilitating searching the database with a query object, the instructions comprising instructions for:

calculating a shape space of the database of N objects;

selecting K key objects from the database that are remote from each other in shape space, and that differ from one another in their respective values of some property field, wherein K is less than N;

calculating a minimal distance between the field associated with each of said K key objects and the respective field associated with every other object in said database; and storing in said database, for each of said K key objects, an ordered list of each database object and its distance from said key object, wherein the instructions for calculating a shape space include instructions for:

choosing an initial set of N objects;

calculating a distance matrix D wherein each element $D_{ij}$ is a minimal metric distance between object i and object j and wherein said object i and said object j are in said initial set of objects;

constructing a metric matrix G from D according to a distance geometry technique;

diagonalizing G, thereby obtaining eigenvalues of G, and obtaining a set of positions in N−1-dimensional space that reproduce the distances in said matrix D to within a tolerance T, wherein each position of said set of positions has N−1 coordinates associated with it;

removing each of the N−1 coordinates that can be set to zero for every object in said set of objects such that a remaining number, M, of the N−1 coordinates still enables said distance matrix to be reproduced to within said tolerance, T; and defining the shape space to be an M dimensional subspace occupied by the N objects;

wherein the database is stored on the computer.

29. A computer configured to search a database with a query object, the computer comprising a memory encoded with instructions that, when executed by the computer:

organize the database according to the method of claim 26;

identify the ordered list of objects associated with the key object calculated to be closest to the query object; and calculate distances between the query object and those objects in the ordered list associated with the key object calculated to be closest to the query object.

30. A non-transitory computer program product comprising a medium encoded with instructions that, when executed by a computer, cause the computer to search a database with a query object, the instructions comprising instructions for:

organizing the database according to the method of claim 26;

identifying the ordered list of objects associated with the key object calculated to be closest to the query object; and calculating distances between the query object and those objects in the ordered list associated with the key object calculated to be closest to the query object.

* * * * *